United States Patent
Wariar et al.

(10) Patent No.: US 9,950,175 B2
(45) Date of Patent: *Apr. 24, 2018

(54) REMOTE CLOSED-LOOP TITRATION OF DECONGESTIVE THERAPY FOR THE TREATMENT OF ADVANCED HEART FAILURE

(71) Applicant: Cardiac Pacemakers, Inc., St. Paul, MN (US)

(72) Inventors: Ramesh Wariar, Blaine, MN (US); Barun Maskara, Blaine, MN (US); Qi An, Blaine, MN (US); Pramodsingh Hirasingh Thakur, Woodbury, MN (US); Julie A. Thompson, Circle Pines, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/604,880

(22) Filed: Jan. 26, 2015

(65) Prior Publication Data

US 2015/0141953 A1    May 21, 2015

Related U.S. Application Data

(63) Continuation of application No. 13/781,258, filed on Feb. 28, 2013, now Pat. No. 8,972,002, which is a (Continued)

(51) Int. Cl.
*A61M 5/172*    (2006.01)
*A61N 1/365*    (2006.01)
(Continued)

(52) U.S. Cl.
CPC ....... *A61N 1/36585* (2013.01); *A61M 5/1723* (2013.01); *A61N 1/3627* (2013.01);
(Continued)

(58) Field of Classification Search
CPC .................. A61M 5/1723; A61N 1/36592
(Continued)

(56) References Cited

U.S. PATENT DOCUMENTS

| 4,094,308 A | 6/1978 | Cormier |
| 4,289,141 A | 9/1981 | Cormier |

(Continued)

OTHER PUBLICATIONS

"U.S. Appl. No. 11/142,851, Examiner Interview Summary filed Dec. 23, 2008", 1 pg.

(Continued)

*Primary Examiner* — Carl H Layno
*Assistant Examiner* — Jon Eric C Morales
(74) *Attorney, Agent, or Firm* — Schwegman Lundberg & Woessner, P.A.

(57) ABSTRACT

An apparatus comprises one or more physiological sensing circuits that generate a sensed physiological signal and at least one of the physiological sensing circuits is implantable, a measurement circuit configured to recurrently measure one or more physiological parameters that indicate a status of heart failure of the subject, a comparison circuit configured to compare the one or more physiological parameter measurements to one or more physiological parameter target values, a therapy circuit configured to control delivery of one or more drugs to treat heart failure, and a control circuit in electrical communication with the comparison circuit and the therapy circuit and configured to recurrently adjust delivery of drug therapy according to the comparison of the measured physiological parameters to the physiological parameter targets.

18 Claims, 8 Drawing Sheets

Related U.S. Application Data continuation-in-part of application No. 13/605,397, filed on Sep. 6, 2012, now Pat. No. 8,535,235, which is a continuation of application No. 13/178,945, filed on Jul. 8, 2011, now Pat. No. 8,277,389, which is a continuation of application No. 12/703,533, filed on Feb. 10, 2010, now Pat. No. 8,007,442, which is a continuation of application No. 11/142,851, filed on Jun. 1, 2005, now Pat. No. 7,670,298.

(51) Int. Cl.
*A61N 1/362* (2006.01)
*A61N 1/37* (2006.01)
*A61N 1/375* (2006.01)

(52) U.S. Cl.
CPC ..... *A61N 1/36564* (2013.01); *A61N 1/36578* (2013.01); *A61N 1/36592* (2013.01); *A61N 1/3702* (2013.01); *A61M 2005/1726* (2013.01); *A61M 2205/054* (2013.01); *A61M 2205/3303* (2013.01); *A61M 2230/20* (2013.01); *A61M 2230/30* (2013.01); *A61M 2230/42* (2013.01); *A61N 1/375* (2013.01)

(58) Field of Classification Search
USPC .......................................... 604/20; 600/301
See application file for complete search history.

(56) References Cited

U.S. PATENT DOCUMENTS

| | | | |
|---|---|---|---|
| 4,446,872 A | 5/1984 | Marsoner et al. | |
| 4,548,204 A | 10/1985 | Groch et al. | |
| 4,649,930 A | 3/1987 | Groch et al. | |
| 4,763,646 A | 8/1988 | Lekholm | |
| 4,905,706 A | 3/1990 | Duff et al. | |
| 4,915,113 A | 4/1990 | Holman | |
| 4,989,611 A | 2/1991 | Zanetti et al. | |
| 5,159,932 A | 11/1992 | Zanetti et al. | |
| 5,365,932 A | 11/1994 | Greenhut | |
| 5,496,361 A | 3/1996 | Moberg et al. | |
| 5,554,177 A | 9/1996 | Kieval et al. | |
| 5,609,612 A | 3/1997 | Plicchi et al. | |
| 5,674,256 A | 10/1997 | Carlson | |
| 5,685,317 A | 11/1997 | Sjostrom | |
| 5,687,738 A | 11/1997 | Shapiro et al. | |
| 5,697,375 A | 12/1997 | Hickey | |
| 5,700,283 A | 12/1997 | Salo | |
| 5,738,102 A | 4/1998 | Lemelson | |
| 5,792,195 A | 8/1998 | Carlson et al. | |
| 5,836,987 A | 11/1998 | Baumann et al. | |
| 5,853,005 A | 12/1998 | Scanlon | |
| 5,991,661 A | 11/1999 | Park et al. | |
| 6,009,349 A | 12/1999 | Mouchawar et al. | |
| 6,026,324 A | 2/2000 | Carlson | |
| 6,044,298 A | 3/2000 | Salo et al. | |
| 6,044,299 A | 3/2000 | Nilsson | |
| 6,045,513 A | 4/2000 | Stone et al. | |
| 6,053,872 A | 4/2000 | Mohler | |
| 6,058,329 A | 5/2000 | Salo et al. | |
| 6,064,910 A | 5/2000 | Andersson et al. | |
| 6,077,227 A | 6/2000 | Miesel et al. | |
| 6,152,884 A | 11/2000 | Bjorgaas | |
| 6,264,611 B1 | 7/2001 | Ishikawa et al. | |
| 6,298,269 B1 | 10/2001 | Sweeney | |
| 6,312,378 B1 | 11/2001 | Bardy | |
| 6,366,811 B1 | 4/2002 | Carlson | |
| 6,368,283 B1 | 4/2002 | Xu et al. | |
| 6,409,675 B1 | 6/2002 | Turcott | |
| 6,415,033 B1 | 7/2002 | Halleck et al. | |
| 6,440,078 B1 | 8/2002 | Curiel et al. | |
| 6,440,082 B1 | 8/2002 | Joo et al. | |
| 6,453,195 B1 * | 9/2002 | Thompson ............... | A61N 1/30 607/3 |
| 6,477,406 B1 | 11/2002 | Turcott | |
| 6,491,639 B1 | 12/2002 | Turcott | |
| 6,527,729 B1 | 3/2003 | Turcott | |
| 6,575,916 B2 | 6/2003 | Halleck et al. | |
| 6,643,548 B1 | 11/2003 | Mai et al. | |
| 6,650,940 B1 | 11/2003 | Zhu et al. | |
| 6,665,564 B2 | 12/2003 | Lincoln et al. | |
| 6,795,732 B2 | 9/2004 | Stadler et al. | |
| 6,810,287 B2 | 10/2004 | Zhu et al. | |
| 6,824,519 B2 | 11/2004 | Narimatsu et al. | |
| 6,830,548 B2 | 12/2004 | Bonnet et al. | |
| 6,839,593 B1 | 1/2005 | Sun et al. | |
| 6,845,263 B2 | 1/2005 | Kawaguchi | |
| 6,963,777 B2 | 11/2005 | Lincoln et al. | |
| 7,039,462 B2 | 5/2006 | Pastore et al. | |
| 7,052,466 B2 | 5/2006 | Scheiner et al. | |
| 7,079,896 B1 | 7/2006 | Park et al. | |
| 7,115,096 B2 | 10/2006 | Siejko et al. | |
| 7,123,962 B2 | 10/2006 | Siejko et al. | |
| 7,174,203 B2 | 2/2007 | Arand et al. | |
| 7,203,541 B2 * | 4/2007 | Sowelam ............... | A61N 1/3627 607/18 |
| 7,634,309 B2 | 12/2009 | Wariar et al. | |
| 7,670,298 B2 | 3/2010 | Carlson et al. | |
| 8,007,442 B2 | 8/2011 | Carlson et al. | |
| 8,043,215 B2 | 10/2011 | Zhang et al. | |
| 8,277,389 B2 | 10/2012 | Carlson et al. | |
| 8,535,235 B2 | 9/2013 | Carlson et al. | |
| 8,755,883 B2 | 6/2014 | Wariar et al. | |
| 8,845,544 B2 | 9/2014 | Carlson et al. | |
| 8,972,002 B2 * | 3/2015 | Wariar ............... | A61N 1/36564 128/200.24 |
| 2002/0001390 A1 | 1/2002 | Kawaguchi | |
| 2002/0035337 A1 | 3/2002 | Oka | |
| 2002/0082645 A1 | 6/2002 | Sweeney | |
| 2002/0091332 A1 | 7/2002 | Bombardini | |
| 2002/0107450 A1 | 8/2002 | Ogura | |
| 2002/0147401 A1 | 10/2002 | Oka | |
| 2002/0151812 A1 | 10/2002 | Scheiner et al. | |
| 2002/0151938 A1 | 10/2002 | Corbucci | |
| 2002/0188329 A1 | 12/2002 | Struble | |
| 2003/0055352 A1 | 3/2003 | Hayek et al. | |
| 2003/0055461 A1 | 3/2003 | Girouard et al. | |
| 2003/0069608 A1 | 4/2003 | Sweeney | |
| 2003/0072458 A1 | 4/2003 | Halleck et al. | |
| 2003/0093002 A1 | 5/2003 | Kuo | |
| 2003/0093003 A1 | 5/2003 | Watrous et al. | |
| 2003/0120159 A1 | 6/2003 | Mohler | |
| 2003/0176896 A1 | 9/2003 | Lincoln et al. | |
| 2003/0208240 A1 | 11/2003 | Pastore et al. | |
| 2003/0216620 A1 | 11/2003 | Jain et al. | |
| 2003/0229289 A1 | 12/2003 | Mohler | |
| 2004/0024423 A1 | 2/2004 | Lincoln et al. | |
| 2004/0039419 A1 | 2/2004 | Stickney et al. | |
| 2004/0039420 A1 | 2/2004 | Jayne et al. | |
| 2004/0064056 A1 | 4/2004 | Ogura | |
| 2004/0078059 A1 | 4/2004 | Ding et al. | |
| 2004/0078060 A1 | 4/2004 | Ding et al. | |
| 2004/0106874 A1 | 6/2004 | Eigler et al. | |
| 2004/0106960 A1 | 6/2004 | Siejko et al. | |
| 2004/0106961 A1 | 6/2004 | Siejko et al. | |
| 2004/0127792 A1 | 7/2004 | Siejko et al. | |
| 2004/0138572 A1 | 7/2004 | Thiagarajan | |
| 2004/0167417 A1 | 8/2004 | Schulhauser et al. | |
| 2004/0204744 A1 | 10/2004 | Penner et al. | |
| 2004/0215264 A1 | 10/2004 | Van Bentem | |
| 2004/0225332 A1 | 11/2004 | Gebhardt et al. | |
| 2004/0230129 A1 | 11/2004 | Haefner | |
| 2004/0236239 A1 | 11/2004 | Murray et al. | |
| 2004/0254481 A1 | 12/2004 | Brodnick | |
| 2004/0254483 A1 | 12/2004 | Zdeblick et al. | |
| 2004/0267147 A1 | 12/2004 | Sullivan | |
| 2004/0267148 A1 | 12/2004 | Arand et al. | |
| 2005/0010257 A1 | 1/2005 | Lincoln et al. | |
| 2005/0027323 A1 | 2/2005 | Mulligan et al. | |
| 2005/0033190 A1 | 2/2005 | Bauer | |
| 2005/0102001 A1 | 5/2005 | Maile et al. | |
| 2005/0115561 A1 * | 6/2005 | Stahmann et al. ....... | 128/200.24 |
| 2005/0119708 A1 | 6/2005 | Haefner | |

(56) References Cited

U.S. PATENT DOCUMENTS

| | | |
|---|---|---|
| 2006/0020294 A1 | 1/2006 | Brockway et al. |
| 2006/0048894 A1 | 3/2006 | Yamazaki et al. |
| 2006/0122651 A1 | 6/2006 | Whitman |
| 2006/0167334 A1 | 7/2006 | Anstadt et al. |
| 2006/0247702 A1 | 11/2006 | Stegemann et al. |
| 2006/0276849 A1 | 12/2006 | Carlson et al. |
| 2006/0282000 A1 | 12/2006 | Zhang et al. |
| 2007/0043299 A1 | 2/2007 | Wariar et al. |
| 2008/0051838 A1* | 2/2008 | Shuros ............ A61F 2/2403 607/2 |
| 2008/0103548 A1* | 5/2008 | Fowler ............ A61N 1/36082 607/45 |
| 2008/0114219 A1* | 5/2008 | Zhang et al. ............ 600/301 |
| 2010/0087890 A1 | 4/2010 | Wariar et al. |
| 2010/0145403 A1 | 6/2010 | Carlson et al. |
| 2011/0263988 A1 | 10/2011 | Carlson et al. |
| 2011/0313491 A1 | 12/2011 | Bange et al. |
| 2012/0330174 A1 | 12/2012 | Carlson et al. |
| 2013/0178786 A1 | 7/2013 | Wariar et al. |
| 2014/0018690 A1 | 1/2014 | Carlson et al. |

OTHER PUBLICATIONS

"U.S. Appl. No. 11/142,851, Final Office Action mailed Jul. 15, 2008", 7 pgs.

"U.S. Appl. No. 11/142,851, Final Office Action mailed Oct. 6, 2008", 7 pgs.

"U.S. Appl. No. 11/142,851, Non-Final Office Action mailed Feb. 7, 2008", 6 pgs.

"U.S. Appl. No. 11/142,851, Non-Final Office Action mailed May 18, 2007", 7 pgs.

"U.S. Appl. No. 11/142,851, Non-Final Office Action mailed May 21, 2009", 7 pgs.

"U.S. Appl. No. 11/142,851, Non-Final Office Action mailed Dec. 19, 2008", 6 pgs.

"U.S. Appl. No. 11/142,851, Notice of Allowance mailed Sep. 27, 2007", 7 pgs.

"U.S. Appl. No. 11/142,851, Notice of Allowance mailed Oct. 6, 2009", 6 pgs.

"U.S. Appl. No. 11/142,851, Response filed Mar. 2, 2009 to Non-Final Office Action mailed Dec. 19, 2008", 7 pgs.

"U.S. Appl. No. 11/142,851, Response filed May 7, 2008 to Non-Final Office Action mailed Feb. 7, 2008", 8 pgs.

"U.S. Appl. No. 11/142,851, Response filed Jun. 23, 2009 to Non Final Office Action mailed May 21, 2009", 15 pgs.

"U.S. Appl. No. 11/142,851, Response filed Aug. 16, 2007 to Non-Final Office Action mailed May 18, 2007", 17 pgs.

"U.S. Appl. No. 11/208,281, Examiner Interview Summary mailed Jan. 29, 2009", 4 pgs.

"U.S. Appl. No. 11/208,281, Final Office Action mailed May 14, 2008", 10 pgs.

"U.S. Appl. No. 11/208,281, Non-Final Office Action mailed Aug. 10, 2007", 9 pgs.

"U.S. Appl. No. 11/208,281, Non-Final Office Action mailed Oct. 28, 2008", 13 pgs.

"U.S. Appl. No. 11/208,281, Notice of Allowance mailed Aug. 4, 2009", 7 pgs.

"U.S. Appl. No. 11/208,281, Response filed Jan. 28, 2009 to Non Final Office Action mailed Oct. 28, 2008", 13 pgs.

"U.S. Appl. No. 11/208,281, Response filed Mar. 3, 2008 to Restriction Requirement mailed Jan. 31, 2008", 11 pgs.

"U.S. Appl. No. 11/208,281, Response filed May 7, 2009 to Restriction Requirement mailed Apr. 16, 2009", 8 pgs.

"U.S. Appl. No. 11/208,281, Response filed Aug. 14, 2008 to Final Office Action mailed May 14, 2008", 19 pgs.

"U.S. Appl. No. 11/208,281, Response filed Nov. 13, 2007 to Non-Final Office Action mailed Aug. 10, 2007", 44 pgs.

"U.S. Appl. No. 11/208,281, Restriction Requirement mailed Jan. 31, 2008", 8 pgs.

"U.S. Appl. No. 11/208,281, Restriction Requirement mailed Apr. 16, 2009", 6 pgs.

"U.S. Appl. No. 12/634,277, Examiner Interview Summary mailed Jun. 19, 2012", 3 pgs.

"U.S. Appl. No. 12/634,277, Examiner interview Summary mailed Nov. 2, 2012", 3 pgs.

"U.S. Appl. No. 12/634,277, Final Office Action mailed Sep. 20, 2012", 14 pgs.

"U.S. Appl. No. 12/634,277, Non Final Office Action mailed Mar. 2, 2012", 10 pgs.

"U.S. Appl. No. 12/634,277, Notice of Allowance mailed Feb. 5, 2014", 10 pgs.

"U.S. Appl. No. 12/634,277, Response filed Jul. 2, 2012 to Non Final Office Action mailed Mar. 3, 2012", 12 pgs.

"U.S. Appl. No. 12/634,277, Response filed Dec. 18, 2012 to Final Office Action mailed Sep. 20, 2012", 12 pgs.

"U.S. Appl. No. 12/703,533, Non-Final Office Action mailed Oct. 1, 2010", 7 pgs.

"U.S. Appl. No. 12/703,533, Notice of Allowance mailed Mar. 24, 2011", 7 pgs.

"U.S. Appl. No. 12/703,533, Notice of Allowance mailed Dec. 7, 2010", 4 pgs.

"U.S. Appl. No. 12/703,533, Preliminary Amendment filed Mar. 3, 2011", 9 pgs.

"U.S. Appl. No. 12/703,533, Response filed Oct. 25, 2010 to Non Final Office Action mailed Oct. 1, 2010", 13 pgs.

"U.S. Appl. No. 13/178,945, Non Final Office Action mailed Mar. 15, 2012", 8 pgs.

"U.S. Appl. No. 13/178,945, Notice of Allowance mailed May 31, 2012", 7 pgs.

"U.S. Appl. No. 13/178,945, Response filed Mar. 27, 2012 to Non Final Office Action mailed Mar. 15, 2012", 10 pgs.

"U.S. Appl. No. 13/605,397, Non Final Office Action mailed Jan. 16, 2013", 8 pgs.

"U.S. Appl. No. 13/605,397, Notice of Allowance mailed May 17, 2013", 8 pgs.

"U.S. Appl. No. 13/605,397, Response filed Apr. 16, 2013 to Non Final Office Action mailed Jan. 16, 2013", 9 pgs.

"U.S. Appl. No. 13/781,258, Non Final Office Action mailed Jun. 18, 2014", 10 pgs.

"U.S. Appl. No. 13/781,258, Notice of Allowance mailed Oct. 22, 2014", 7 pgs.

"U.S. Appl. No. 13/781,258, Response filed Sep. 4, 2014 to Non Final Office Action mailed Jun. 18, 2014", 13 pgs.

"U.S. Appl. No. 14/024,363, Response filed Feb. 27, 2014 to Non Final Office Action mailed Nov. 27, 2013", 9 pgs.

"U.S. Appl. No. 14/024,363, Non Final Office Action mailed Nov. 27, 2013", 9 pgs.

"U.S. Appl. No. 14/024,363, Notice of Allowance mailed May 29, 2014", 8 pgs.

Bombardini, Tonino, et al., "A New Intravacitary Catheter for Monitoring Contractility Through Endocardially Recorded First Heart Sound: Initial Clinical Validation", JACC, (Feb. 1995), 1 pg.

Bongiorni, M. G, et al., "Is local myocardial contractility related to endocardial acceleration signals detected by a transvenous pacing lead?", Pacing Clin Electrophysiol, (11 Pt 2), (Nov. 1996), 1682-1688.

Dubrey, S. W., "Home inotrope treatment for intractable heart failure following heart transplantation", Heart; 82, (1999), 248-252.

Jaski, B. E., "Chapter 3—Circulation, Part 1: The Problem of Heart Failure", Basics of Heart Failure: A Problem Solving Approach, Kluwer Academic Publishers, Norwell, MA, (2000), 25-52.

Little, William C, et al., "Assessment of Normal and Abnormal Cardiac Function", Heart Disease: A Textbook of Cardiovascular Medicine, W.B. Saunders, Philadelphia PA, (2001), 479-502.

Mabo, Philippe, et al., "Surface SonR Signal: A New Tool for Non Invasive Estimation of Systolic and Diastolic Time Intervals in CRT Patients", Abstract HRS09L_4554, (May 15, 2009), 1 pg.

Tassin, Aude, et al., "Correlation in Amplitude Between First Heart Sound and First SonR Signal (SonR1)", Abstract HRS09L_4099, (May 15, 2009), 2 pgs.

(56) References Cited

OTHER PUBLICATIONS

Wariar, Ramesh, et al., "Tracking Progression of Congestive Heart Failure Via a Force-Frequency Relationship", U.S. Appl. No. 11/208,281, filed Aug. 19, 2005, 41 pgs.

* cited by examiner

REMOTE CLOSED-LOOP TITRATION OF DECONGESTIVE THERAPY FOR THE TREATMENT OF ADVANCED HEART FAILURE

CROSS REFERENCE TO RELATED APPLICATIONS

This application is a continuation of U.S. application Ser. No. 13/781,258, filed Feb. 28, 2013, now issued as U.S. Pat. No. 8,972,002, which is a continuation-in-part of U.S. application ser. No. 13/605,397, filed Sep. 6, 2012, now issued as U.S. Pat. No. 8,535,235, which is a continuation of U.S. application Ser. No. 13/178,945, filed Jul. 8, 2011, now issued as U.S. Pat. No. 8,277,389, which is a continuation of U.S. application Ser. No. 12/703,533, filed Feb. 10, 2010, now issued as U.S. Pat. No. 8,007,442, which is a continuation of U.S. application Ser. No. 11/142,851, filed Jun. 1, 2005, now issued as U.S. Pat. No. 7,670,298, each of which is hereby incorporated by reference in its entirety.

TECHNICAL FIELD

This document relates to cardiac rhythm management devices generally, and more particularly to cardiac rhythm management devices that employ a sensing device to detect a heart sound and to extract morphological data therefrom, in order to relate the heart sound to a hemodynamic metric.

BACKGROUND

Cardiac pacemakers generally provide functions including sensing electrical signals generated by the heart, controlling stimulation of excitable tissues in the heart, sensing the response of the heart to such stimulation, and responding to inadequate or inappropriate stimulus or response (e.g., dysrhythmia) to deliver therapeutic stimuli to the heart. Some pacemakers employ cardiac resynchronization therapy. Some existing cardiac pacemakers also function to communicate with an external programmer device to support a variety of monitoring, diagnostic and configuration functions.

Certain cardiac pacemakers, defibrillators with pacing and/or cardiac resynchronization therapy (CRT) capabilities, and CRT devices (collectively referred to herein by the term "pacemaker") include an internal accelerometer for measuring the level of activity of the patient (e.g., movement caused by walking around, or by muscle twitches). Such pacemakers process (e.g., filter) the accelerometer signal to reduce noise interfering with the measurement of the patient's motion-related activity, such as the sounds generated by the heart itself, and then use the processed signals as inputs to one or more algorithms for generating the signals used to control the stimulation of the heart. For example, if the accelerometer indicates that a patient is walking briskly, the pacemaker may stimulate the heart to beat at a faster rate (often subject to an upper rate limit) than when the patient is at rest.

Pacemakers are typically electrically coupled to a patient's heart by a lead system. The lead system may include one or multiple leads that may provide electrical contact with one or multiple chamber of a patient's heart. Some leads may contain an accelerometer at their distal end. When implanted, the accelerometer is located within a patient's heart, and may detect sounds emitted by the heart. Such a scheme may be used, for example, to detect an S1 heart sound (an S1 heart sound is the first sound made by the heart during a cardiac cycle). It is known that an S1 heart sound contains data content related to left ventricular contractility, a characteristic of the heart that reveals the capacity of the myocardium to shorten, and therefore to circulate blood through the body. A pacemaker system such as the one described may measure S1 heart sounds as a means to gather information about the contractility of the patient's heart.

The above-described scheme exhibits certain shortcomings, however. Such a scheme may lead to the use of two accelerometers—an internal accelerometer for use in adjusting the pacing rate during instances of physical exertion by the patient, and an external accelerometer situated in the heart for the purpose of monitoring heart sounds. Disposing an accelerometer on the tip of a lead is costly, and could be avoided if an internal accelerometer could be used to detect heart sounds with a sufficient signal-to-noise ratio to permit extraction of data content related to cardiac performance (such as left ventricular contractility).

SUMMARY

Against this backdrop the present invention was developed. According to one embodiment, an implantable device includes a transducer that converts heart sounds into an electrical signal. A control circuit is coupled to the transducer. The control circuit is configured to receive the electrical signal, identify an S1 heart sound, and convert the S1 heart sound into morphological data that relates to a rate of change of pressure within a ventricle of a heart. A housing encloses the control circuit. The transducer is located in a region in or on the housing.

According to another embodiment, a method includes using a transducer located outside of a heart to detect an S1 heart sound. The S1 heart sound is converted into an electrical signal using the transducer. Morphological data is extracted from the electrical signal. The morphological data relates to a rate of change of pressure within a ventricle of the heart.

According to yet another embodiment, a system includes an implantable device and an external system. The implantable device includes a transducer located in or on the implantable device. The transducer is configured to convert heart sounds into an electrical signal. A first control circuit is coupled to the transducer, and is configured to receive the electrical signal. The implantable device also includes a first interface circuit for communicating with the external system. The external system includes a second interface circuit for communicating with the implantable device. A second control circuit is coupled to the second interface circuit. The first and second control circuits cooperate to identify an S1 heart sound, and to generate morphological data from the S1 heart sound. The morphological data relates to a rate of change of pressure in a ventricle of a heart.

DETAILED DESCRIPTION

During the course of a cardiac cycle, blood flows from the peripheral venous system to the right atrium. From the right atrium, blood passes through the tricuspid valve to the right ventricle. Blood exits the right ventricle, through the pulmonic valve, into the pulmonary artery, and is directed through the lungs, so that the blood may be reoxygenated. Oxygenated blood from the lungs is drawn from the pulmonary vein to the left atrium. From the left atrium, blood passes though the mitral valve to the left ventricle. Finally, the blood flows from the left ventricle, through the aortic valve, to the peripheral arterial system in order to transfer oxygenated blood to the organs of the body.

As the blood circulates and the various valves open and close (as just described), certain heart sounds are produced. The heart sounds occur in a fixed sequence and are respectively referred to as S1, S2, S3 and S4.

The S1 heart sound is caused by acceleration and deceleration of blood, and closure of the mitral and tricuspid valves. The S1 heart sound generated during a given cardiac cycle exhibits morphological characteristics that relate to the maximum rate of change of pressure in the left ventricle during the given cardiac cycle. The maximum rate of change of pressure in the left ventricle is related to, and may be used as a proxy measurement for, left ventricular contractility. Left ventricular contractility is important, because it indicates the capacity of the left ventricle to contract, and therefore to circulate blood through the peripheral arterial system.

Heart sounds can include components of the S1, S2, S3 and S4 heart sounds such as the aortic component of S2 ("A2"), the pulmonary component of S2 ("P2"), or other broadband sounds or vibrations associated with mechanical activity of the heart, such as valve closures or fluid movement (e.g., a heart murmur, etc.).

Figure 1:
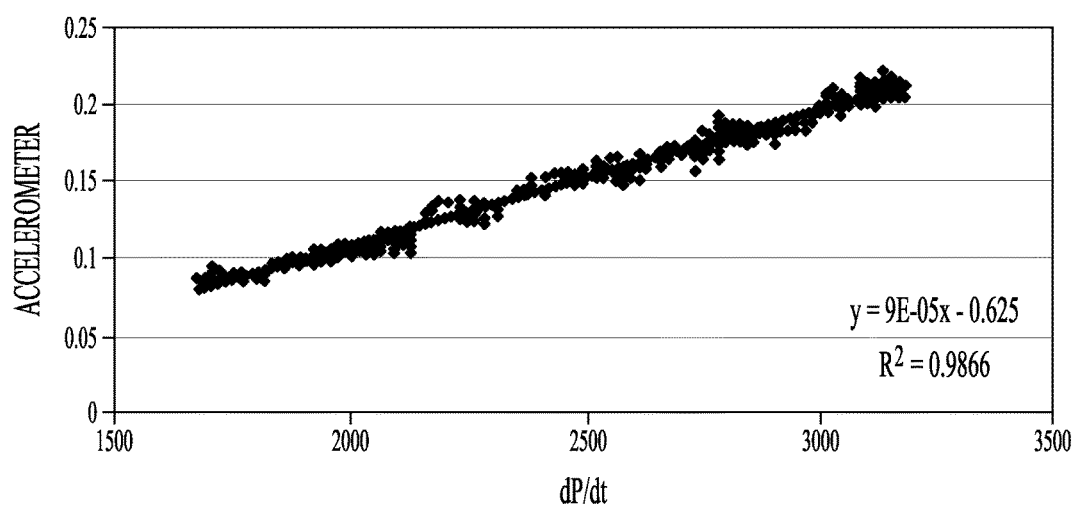
FIG. 1 depicts data supporting the notion that the S1 heart sound contains certain data content related to maximum rate of change of left ventricular pressure.

FIG. 1 depicts data illustrating that the S1 heart sound contains certain data content related to maximum rate of change of left ventricular pressure. FIG. 1 presents a chart having an x-axis and a y-axis. Maximum rate of change of left ventricular pressure for a given cardiac cycle is measured along the x-axis in units of millimeters of mercury per second (mmHg/s). Median peak-to-peak amplitude exhibited by S1 heart sounds over the past N cardiac cycles is measured along the y-axis in units of mG, where N is on the order of 10, for example, between 5 and 25. (One scheme by which "median peak-to-peak amplitude" is determined is discussed below).

To obtain the data presented in FIG. 1, animal testing was performed. During the test, the animal was at rest, and its left ventricular filling pressure was monitored and determined to be constant. Over a span of time, a drug known to modify myocardial contractility was administered. At intervals, the animal's maximum rate of left ventricular pressure change was measured, and was mated with the median peak-to-peak amplitude exhibited by S1 heart sounds over the past N=approximately 10 (5-25) cardiac cycles, as measured by an accelerometer located at a point remote from the animal's heart. (The accelerometer was located within a cardiac rhythm management device implanted in the animal). Further, the accelerometer data was signal conditioned (discussed below) prior to measurement of the peak-to-peak amplitude. Thus, a given data point on the chart of FIG. 1 is determined by the maximum rate of left ventricular pressure change during a given cycle, and the median peak-to-peak amplitude exhibited by S1 heart sounds over the past N cardiac cycles.

As can be seen from FIG. 1, the median peak-to-peak amplitude exhibited over a span of cardiac cycles increases (approximately linearly) with the maximum rate of left ventricular pressure change. Therefore, by measuring the median peak-to-peak amplitude exhibited over a span of N cardiac cycles, the maximum rate of left ventricular pressure change may be determined.

Figure 2:
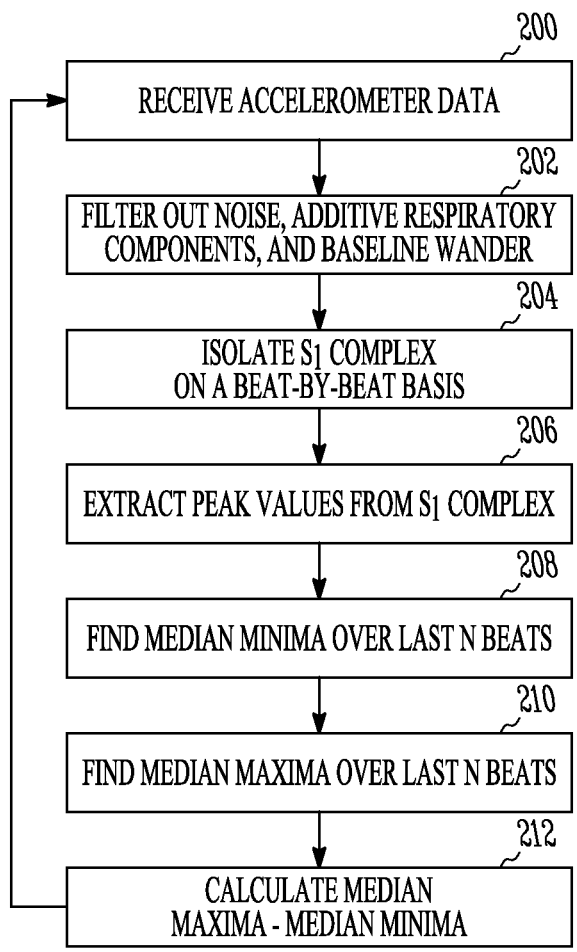
FIG. 2 depicts a method of analyzing accelerometer data to determine a morphological characteristic related to a hemodynamic metric, according to some embodiments of the present invention.

Accordingly, FIG. 2 illustrates a method useful in arriving at data indicative of left ventricular contractility. The example of FIG. 2 begins with the reception of raw accelerometer data, as shown in operation 200. Thereafter, the raw accelerometer data is conditioned (discussed below), for example, to remove noise, respiratory components, and baseline wander (operation 202). The resulting data stream substantially represents the sounds emitted by the heart.

Figure 3A:
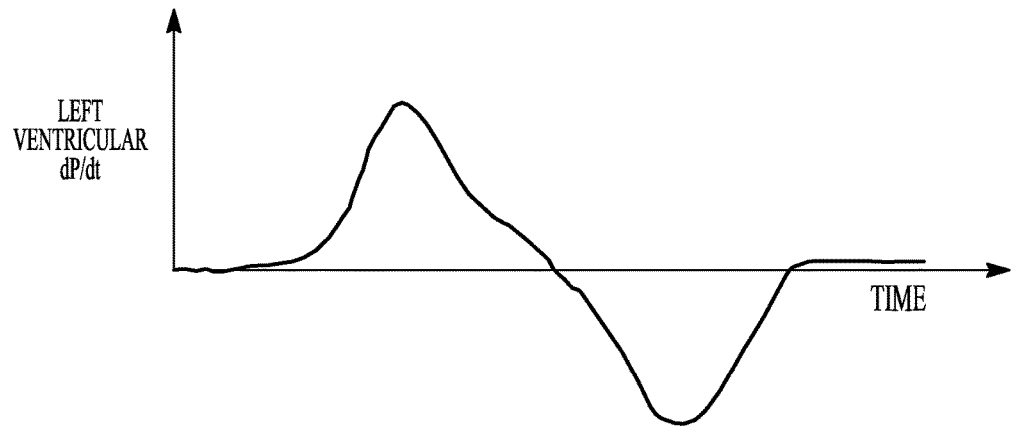
FIG. 3A depicts a chart presenting rate of change in left ventricular pressure (y-axis) versus time (x-axis).
Figure 3B:
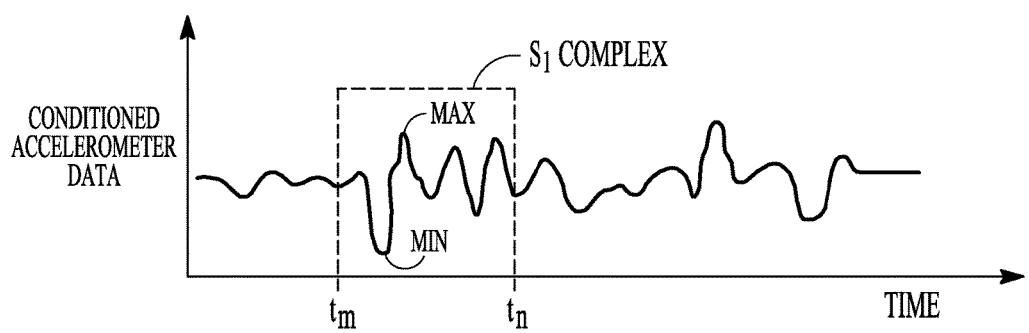
FIG. 3B depicts a chart presenting conditioned accelerometer data (y-axis) versus time (x-axis).

This conditioned signal is then processed so as to isolate the S1 complex, as shown in operation 204. The result of such a process is depicted in FIG. 3B. FIG. 3B presents conditioned accelerometer data (y-axis) versus time (x-axis). FIG. 3A presents rate of change in left ventricular pressure (y-axis) versus time (x-axis).

FIG. 3B contains a region identified by a dashed box. The dashed box identifies the S1 complex. The process of isolating the S1 complex refers to identifying a point in time $t_m$ at which the S1 complex begins and a point in time $t_n$ at which the S1 complex ends.

Returning to FIG. 2, after isolation of the S1 complex at operation 204, peak values are extracted at operation 206. For example, the exemplary isolated S1 complex depicted in FIG. 3B contains a global maxima labeled "Max," and a global minima labeled "Min." The minima and maxima are "global" over the span of time between $t_m$ and $t_n$. The combined result of operations 200-206 is that, for each cardiac cycle, the amplitude values at each global maxima and minima exhibited by an S1 heart sound are extracted and stored in a manner to preserve their relationship to the cardiac cycle from which they were extracted.

Next, in operations 208 and 210, the median minima and the median maxima exhibited over the last N cardiac cycles are found. For example, assuming that the peak values had been extracted from the $J^{th}$ cardiac cycle in a given instance of execution of operation 206, then operations 208 and 210 yield the median minima and the median maxima exhibited over cardiac cycles J−N+1 through J.

Finally, in operation 212, the median minima determined in operation 208 is subtracted from the median maxima determined in operation 210. The result of operation 212 is an example of a "median peak-to-peak-amplitude," as referred to above with reference to FIG. 1.

Figure 4:
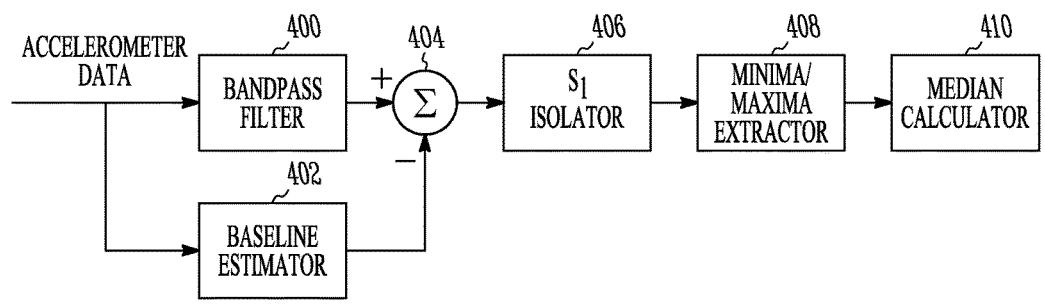
FIG. 4 depicts a signal flow scheme that may be used to implement the method of FIG. 2, according to some embodiments of the present invention.

FIG. 4 depicts a signal flow scheme that may be used to implement the method of FIG. 2. As can be seen from FIG. 4, raw accelerometer data is supplied to both a bandpass filter 400 and a baseline estimator 402. The bandpass filter 400 is characterized by upper and lower cutoff frequencies that are set to pass frequency content included in heart sounds. In one example, the lower and upper cutoff frequencies are approximately 10 Hz and 50 Hz, respectively. The cutoff frequencies are also set to reject frequency content due to movement of the patient (e.g., walking or muscular twitching), and to pass frequency content of the heart sounds.

Typically, the upper and lower cutoff frequencies of a bandpass filter (such as bandpass filter 400) are determined by two sets of poles. A first set of poles determines the lower cutoff frequency (e.g., placement of poles at 10 Hz generates a lower cutoff frequency at approximately 10 Hz). Similarly, a second set of poles determines the upper cutoff frequency (again, placement of poles at 50 Hz generates an upper cutoff frequency at approximately 50 Hz). In order to yield a narrow passband region, the sets of poles determining the upper and lower cutoff frequencies may be oriented in proximity to one another (i.e., the poles may be "squeezed" together). Unfortunately, such an approach tends to exhibit a drawback: the filter may ring when driven by signals with sharp transitions. Since S1 heart sounds tend to exhibit sharp transitions, the bandpass filter 400 may ring if its passband is narrowed by way of "squeezing" its poles close together.

To address the problem of ringing, the baseline estimator 402 is introduced. The baseline estimator 402 yields an estimate of a low-frequency baseline upon which the heart sounds in the accelerometer data are riding. For example, baseline estimator 402 may be an exponentially-weighted historical averaging unit. By subtracting the baseline estimate yielded by the estimator 402 from the output of the bandpass filter 400 (using the subtracting unit 404), unwanted low-frequency content is removed from the signal passed by the filter 400. This means that the lower cutoff frequency of the filter 400 may be relaxed (i.e., set at a relatively lower frequency), and that the combined functioning of the baseline estimator 402 and subtraction unit 404 will remove low frequency content. By relaxing the lower cutoff frequency of the filter, the frequency space between the sets of poles may also be broadened, diminishing the likelihood of ringing in the filter 400.

The combined functioning of passband filter 400, baseline estimator 402, and subtraction unit 404 operate to achieve the effect described with reference to operation 202 in FIG. 2. Thus, the signal yielded by subtraction unit 404 primarily includes content related to heart sounds.

The signal from the subtraction unit 404 is passed to an S1 isolator unit 406, which functions to achieve the result described with reference to operation 204 in FIG. 2. An exemplary method for automatically processing accelerometer signals to isolate S1, S2, and S3 heart sounds is disclosed in U.S. Pat. No. 5,792,195, issued to Carlson et al. on Aug. 11, 1998, which is incorporated by reference herein in its entirety.

The output of the S1 isolator unit 406 is a set of time-sequenced data representing an S1 heart sound. Such data is passed to a minima/maxima extractor 408 to find the global minima and maxima of the S1 complex, as described with reference to operation 206 in FIG. 2.

Finally, the output of the minima/maxima extractor 408 is passed to a median calculator 410 to find the median minima and median maxima exhibited by the last N S1 heart sounds, as described with reference to operations 208 and 210 in FIG. 2.

Returning briefly to FIG. 1, a formula presented therein describes a linear regression of the data contained in the graph. (In the case of the data presented in FIG. 1, the formula is y=0.00009x−0.0625). The "reliability" of the linear regression is indicated by $R^2$, which is a measure of the variance explained by the regression model (in the case of the data presented in the graph of FIG. 1, $R^2$=0.9866). In one example, the reliability of the data is improved (and therefore the reliability of the linear regression model, as understood by $R^2$ is improved) by performing the data processing schemes of FIGS. 2-4 upon heart sounds obtained during periods of exhalation; accelerometer data obtained from heart sounds occurring during periods of inhalation is ignored. To distinguish periods of exhalation and inhalation, transthoracic impedance may be examined (transthoracic impedance may decrease during exhalation, for example).

Figure 5:
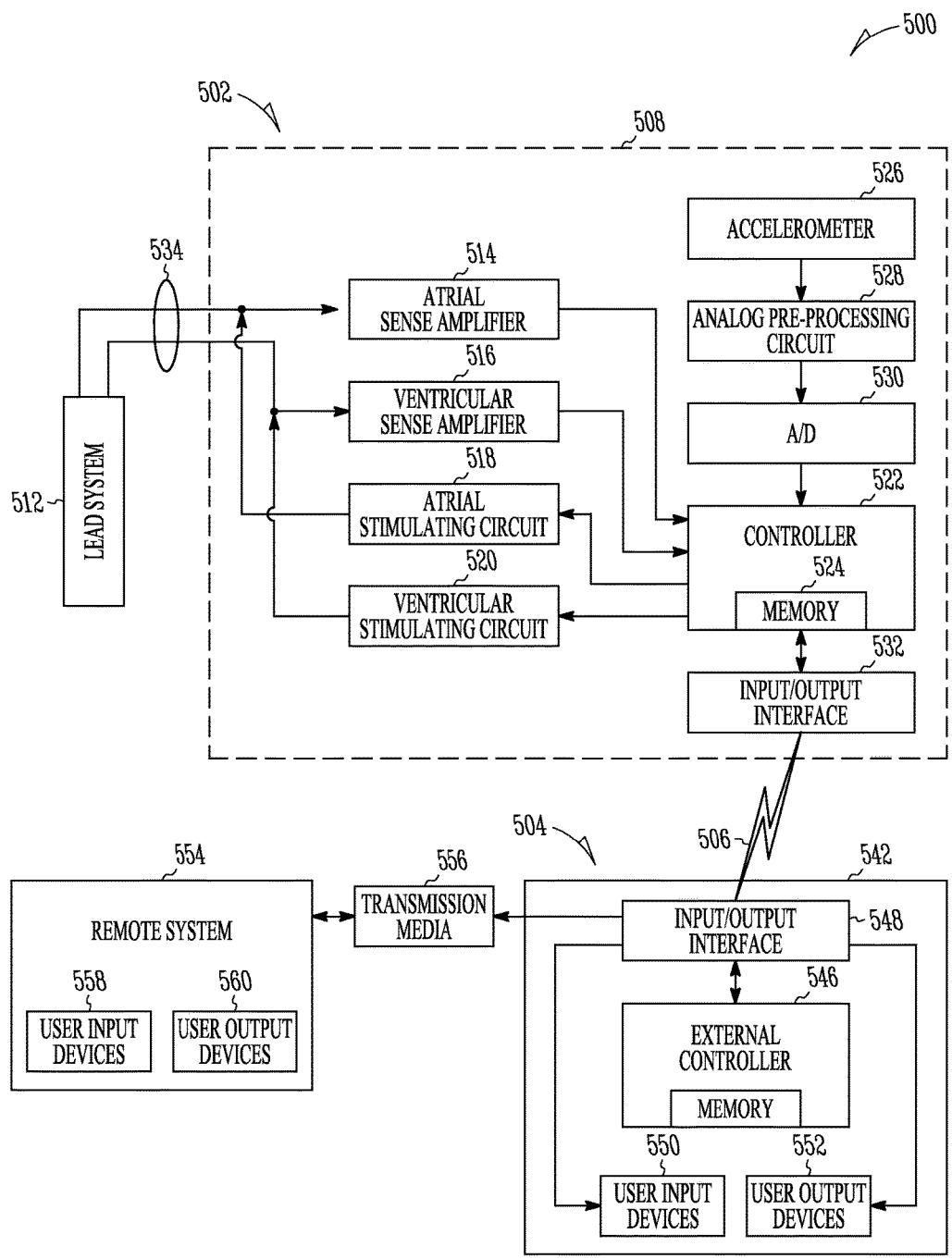
FIG. 5 depicts an exemplary system for performance of the methods and schemes disclosed herein.

FIG. 5 depicts an exemplary system useful for detecting S1 heart sounds, and extracting therefrom one or more morphological characteristics related to left ventricular contractility.

In FIG. 5, an exemplary system 500 for detecting and processing heart sounds includes an implantable system 502 and an external system 504. The implantable system 502 and external system 504 are configured to communicate via a communications link 506.

The implantable system 502 includes an implantable device 508 operatively coupled to a patient's heart by a lead system 512. The components of the implantable device 508 include an atrial sense amplifier 514, a ventricular sense amplifier 516, an atrial stimulating circuit 518, a ventricular stimulating circuit 520, a control circuit or controller 522, a memory 524, an accelerometer 526, an analog pre-processing circuit 528, an analog-to-digital (A/D) converter 530, and an input/output (I/O) interface 532. The components of implantable device 508 are housed within an implantable housing (indicated by the broken lined box in FIG. 5), which may be implanted within the patient's chest cavity (e.g., in the pectoral region) or elsewhere.

The atrial sense amplifier 514, ventricular sense amplifier 516, atrial stimulating circuit 518 and ventricular stimulating circuit 520 are operatively coupled to lead system 512 via a pair of conductors 534. The lead system 512 may include an atrial sensing electrode and an atrial stimulating electrode adapted to be disposed in the right atrial chamber of heart and a ventricular sensing electrode and a ventricular stimulating electrode adapted to be disposed in the right ventricular chamber of the heart.

Sensed atrial and ventricular electrical signals generated by the sensing electrodes are applied to the atrial and ventricular sense amplifiers 514 and 516, respectively. Similarly, atrial and ventricular stimulating signals generated by the atrial and ventricular stimulating circuits 518 and 520 are applied to the atrial and ventricular stimulating electrodes, respectively. The atrial sense amplifier 514, ventricular sense amplifier 516, atrial stimulating circuit 518, and ventricular stimulating circuit 520, are each also operatively coupled to the controller 522.

In other embodiments, other sensing electrode configurations are used for internally sensing one or more electrical signals of heart. In one example, only one sensing electrode may be used. Alternatively, one or more electrodes placed within the body but outside of the heart are used for sensing cardiac electrical signals. In yet another example, a sensing electrode is placed on the implantable housing. In each of these examples, the sensing electrodes are operatively coupled to the controller 522.

In the embodiment shown in FIG. 5, the sensing electrodes and the stimulating electrodes are disposed in the right side of heart. In other embodiments, one or more sensing electrode(s) and one or more stimulating electrode(s) are disposed in the left side of the heart (in lieu of being disposed in the right side of the heart, or in addition to sensing electrode(s) and stimulating electrode(s) disposed in the right side of the heart). The addition of left heart sensing may advantageously allow for the resolution of ambiguities due to disassociation of right and left heart conduction.

The controller 522 can include a microcontroller or microprocessor which can be configured (e.g., by executing a program stored in a read-only memory (ROM) portion of a memory unit 524 and reading and writing data to and from a random access memory (RAM) portion of the memory unit 524) to process the atrial and ventricular electrical signals from the atrial and ventricular sense amplifiers 514 and 516, and to provide control signals to the atrial and ventricular stimulating circuits 518 and 520. In response, the stimulating circuits 518 and 520 provide stimulating pulses to heart via atrial and ventricular stimulating electrodes at appropriate times. In other embodiments, the controller 522 may include other types of control logic elements or circuitry to perform the functions described herein.

The implantable device 508 may be referred to as a dual-chamber pacemaker since pacemaking functions are provided to both atrial and ventricular chambers of heart. In another embodiment, the implantable system includes a single-chamber pacemaker that senses electrical signals and provides stimulating pulses to a single chamber of heart. In yet another embodiment, the implantable system does not provide any stimulation of heart tissues, but includes one or more sensing electrodes for sensing one or more electrical signals of heart, and for providing corresponding sensed signals to controller 522. In still another embodiment, the implantable system does not provide any sensing electrodes for sensing any cardiac electrical signals, but is configured to sense and transmit signals representing heart sounds using a sensor such as the accelerometer 526, as described below.

In the remainder of this description, the implantable device 508 is described as a dual-chamber pacemaker for the sake of illustration. It is to be understood, however, that implantable system 502 need not provide the stimulation functions described herein, and may provide other functions which are not described herein.

In some embodiments, a minute ventilation output channel and a minute ventilation input channel may be interposed between the controller 522 and the ventricular lead. The minute ventilation output channel generates a high-frequency, low-voltage signal that is transmitted from the ventricular lead (in either unipolar or bipolar mode). The input channel receives and conditions the signal. The content of the conditioned signal reveals respiration information.

An accelerometer 526 may be configured to provide sensed signals to the analog pre-processing circuit 528, which generates an analog output signal which is digitized by A/D converter 530. The digitized accelerometer signal is received by the controller 522. In the embodiment of FIG. 5, the accelerometer 526 is located within the housing of implantable device 508. In another embodiment, the accelerometer 526 is located on the housing of the implantable device. The accelerometer 526 may include, for example, a piezo-electric crystal accelerometer sensor of the type used by pacemakers to sense the level of activity of the patient, or may include other types of accelerometers. To detect heart sounds, other types of sound-detecting sensors or microphones may also be used, such as a pressure sensor or a vibration sensor configured to respond to sounds made by the heart.

In another embodiment, the system 500 includes two or more sound-detecting sensors. In such an embodiment, the plurality of sensed heart sound signals from the plurality of sensors may be individually transmitted to external system 504 for display as individual traces, may be combined (e.g., averaged) by external system 504 before being displayed as a single trace, or may be combined by controller 522 before being transmitted to external system 504 as a single heart sound signal. These sensors may include different types of sensors, sensors that are located in different locations, or sensors that generate sensed signals which receive different forms of signal processing.

In one embodiment, the accelerometer 526 is configured to generate sensed signals representative of two distinct physical parameters: (1) the level of activity of the patient; and (2) the heart sounds generated by heart. Accordingly, the analog pre-processing circuit 528 is configured to pre-process the sensed signals from the accelerometer 526 in a manner which conforms to the signal characteristics of both of these physical parameters. For example, if the frequencies of interest for measuring the patient's level of activity are below 10 Hz, while the frequencies of interest for detecting heart sounds are between 0.05 Hz and 50 Hz, then analog pre-processing circuit 528 may include a low-pass filter having a cutoff frequency of 50 Hz. The controller 522 may then perform additional filtering in software, as described above with reference to FIGS. 2-4, for example. Along with filtering, analog pre-processing circuit 528 may perform other processing functions including automatic gain control (AGC) functions.

The analog pre-processing circuit 528 may perform the filtering and baseline wander removal functions described with reference to operation 202 (FIG. 2) and may include modules 400, 402, and 404 (shown in FIG. 4). Alternatively, the analog pre-processing circuit 528 may simply provide automatic gain control functionality.

In some embodiments, the controller 522 performs one or more of steps 204-212 (FIG. 2), and may include one or more of modules 406-410 (FIG. 4). In the context of an embodiment in which the analog pre-processing circuit 528 performs only automatic gain control, the controller may perform operations 200 and 202 (FIG. 2), and may include modules 400-404 (FIG. 4). As discussed below, any operations 200-212 or modules 400-410 to be performed digitally by a controller may be performed cooperatively by the controller 522 within the implantable device 508 and another controller. For example, the controller 522 in the implantable device 508 may perform operation 204, and communicate the result to an external controller (contained in a programmer, for example) that performs operation 206-212. Alternatively, an external controller may perform all of the operations 200 described in FIG. 2.

In another embodiment, the implantable device 508 has two pre-processing channels for receiving sensed signals from accelerometer 526. In still another embodiment, implantable device 508 includes two accelerometers, with one accelerometer configured to generate sensed signals representative of the level of activity of the patient and the other accelerometer configured to generate sensed signals representative of heart sounds. In these latter two embodiments, any hardware and/or software processing performed on the sensed signals can conform to the specific characteristics of the respective sensed signals. For example, the analog pre-processing circuit used for the level-of-activity sensed signals can provide a low-pass filter with a cutoff frequency of 10 Hz, while the analog preprocessing circuit for the heart-sound sensed signals can provide a band-pass filter with cutoff frequencies of 0.05 and 50 Hz. In the latter case, each accelerometer can be selected, located and/or oriented to maximize the detection of the respective physical parameter. In yet another embodiment, if the implantable device does not need to sense the level of activity of the patient, the accelerometer 526 may measure only the sounds made by heart.

The controller 522 is capable of bi-directional communications with an external system 504 via an I/O interface 532. In one embodiment, the I/O interface 532 communicates using RF signals, which may be understood to include inductive coupling. In other embodiments, the I/O interface 532 communicates using optical signals, or a combination of RF and optical signals (e.g., RF signals for receiving data from the external system 504 and optical signals for transmitting data to external system 504, or vice-versa). The controller 522 uses the I/O interface 532 for bi-directional communications with the external system 504 to support conventional monitoring, diagnostic and configuration pacemaker functions. The controller 522 may also use the I/O interface 532 to telemeter data representative of the heart sounds sensed by accelerometer 526 to the external system 504. In various embodiments, the controller 522 further uses the I/O interface 532 to telemeter data representative of cardiac electrical signals (i.e., electrogram or EGM signals), which may include data representative of atrial electrical signals, sensed by the atrial sensing electrode, and/or data representative of ventricular electrical signals, sensed by the ventricular sensing electrode. Thus, implantable system 502 is capable of sensing heart sounds, atrial electrical signals and ventricular electrical signals, and of telemetering data representative of the heart sounds and/or cardiac electrical signals to external system 504. In other embodiments, the controller 522 telemeters data representative of cardiac electrical signals which were sensed by other configurations of internal cardiac sensing electrodes.

The external system 504 may include an external device 542. The external device 542 may include an external controller 546, an I/O interface 548, user input device(s) 550, and user output device(s) 552. Using the I/O interface 548, the external controller 546 is configured for bi-directional communications with the implantable device 508, for receiving input signals from input device(s) 550, and for applying control signals to output device(s) 552. The input device(s) 550 include at least one input device which allows a user (e.g., a physician, nurse, medical technician, etc.) to generate input signals to control the operation of external device 542, such as at least one user-actuatable switch, knob, keyboard, pointing device (e.g., mouse), touch-screen, voice-recognition circuit, etc. The output device(s) 552 include at least one display device (e.g., CRT, flat-panel display, etc.), audio device (e.g., speaker, headphone), or other output device which generates user-perceivable outputs (e.g., visual displays, sounds, etc.) in response to control signals. The external controller 546 may be configured to receive the data representative of heart sounds, atrial electrical signals and/or ventricular electrical signals from implantable system 502, and to generate control signals that, when applied to output device(s) 552, cause the output device(s) to generate outputs that are representative of the heart sounds, the atrial electrical signals and/or the ventricular electrical signals.

The external controller 546 may cooperate with the internal controller 522 to perform any or all of the steps in FIG. 2. For example, the implantable device 508 may telemeter conditioned accelerometer data (yielded from operation 202 in FIG. 2) to the external controller 546 via the communication link 506. The external controller 546 may perform operations 204-212 upon the telemetered data.

In one embodiment, the system 500 further includes a remote system 554 operatively coupled to communicate with the external system 504 via transmission media 556. The remote system 554 includes one or more user input device(s) 558, and one or more user output device(s) 560, which allow a remote user to interact with remote system 554. The transmission media 556 includes, for example, a telephone line, electrical or optical cable, RF interface, satellite link, local area network (LAN), wide area network (WAN) such as the Internet, etc. The remote system 554 cooperates with external system 504 to allow a user located at a remote location to perform any of the diagnostic or monitoring functions that may be performed by a user located at external system 504. For example, data representative of heart sounds and/or cardiac electrical signals are communicated by the external system 504 to the remote system 554 via the transmission media 556 to provide a visual display and/or an audio output on the output device(s) 560, thereby allowing a physician at the remote location to aid in the diagnosis of a patient. The system 554 is "remote" in the sense that a user of remote system 554 is not physically capable of actuating input device(s) 550 and/or of directly perceiving outputs generated by output device(s) 552. For example, the system 554 may be located in another room, another floor, another building, another city or other geographic entity, across a body of water, at another altitude, etc., from the external system 504.

Although not depicted in FIG. 5, the I/O interface 532 may establish a communication link with a communication device in physical proximity to the patient. For example, the I/O interface may establish a data link with a personal digital assistant, and may upload or download any of the data mentioned previously or hereafter. The personal digital assistant may, in turn, establish a link with an access point, so that the link may be effectively extended over a network, such as the Internet.

To this point, the disclosure has discussed schemes for detecting a heart sound, generating morphological data from the heart sound, and relating the morphological data to a hemodynamic metric (FIGS. 1-4). The disclosure has also discussed an exemplary device and system for performing such acts (FIG. 5). The remainder of the disclosure relates to methods which may make use of the methods discussed with reference to FIG. 1-4, and may make use of the exemplary device or system disclosed with reference to FIG. 5.

Figure 6:
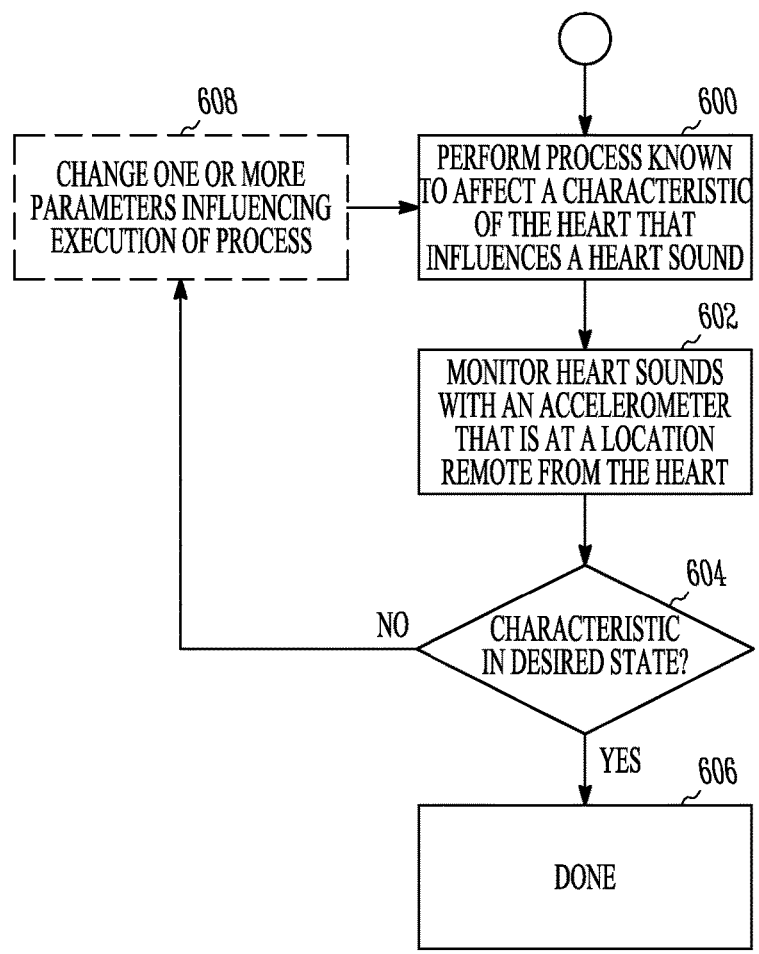
FIG. 6 depicts a method of adjusting parameters that influence a process, according to some embodiments of the present invention.

FIG. 6 depicts a method of adjusting parameters that influence a process. Any of the acts depicted in FIG. 6 may be performed by any controller in the exemplary system of FIG. 5. The method begins with performing a process known to affect a characteristic of the heart that influences sound, as shown in operation 600. For example, operation 600 may include titration of a drug known to influence a heart sound. An inotrope, for instance, enhances the inotropic state of the heart, resulting in greater myocardial contractility, which influences the S1 heart sound (as shown in FIG. 1). Alternatively, operation 600 may include administration of therapy to the heart. For instance, an implantable device (such as the one shown in FIG. 5) may administer cardiac resynchronization therapy to the heart. Over time, cardiac resynchronization therapy may make the heart stronger, resulting in greater myocardial contractility. Again, contractility is known to influence the S1 heart sound.

Next, in operation 602, the heart sounds are detected using an accelerometer that is located at a point that is remote from the heart (e.g., within an implantable device, such as the one depicted in FIG. 5). The monitoring operation 602 may include, for example, performing the acts discussed with reference to FIGS. 2-4. Thus, the median peak-to-peak amplitude exhibited by S1 heart sounds may be monitored (after being conditioned, as discussed with reference to FIGS. 2-4) to obtain information regarding the contractility of the left ventricle.

After monitoring the heart sounds in operation 602, it is determined whether the cardiac characteristic known to relate to the heart sound is in the desired state. For example, in the context of monitoring S1 heart sounds during administration of cardiac resynchronization therapy, the goal may be to increase or maximize contractility of the heart by administration of such therapy. Accordingly, operation 604 may involve a determination of whether the contractility of the heart has been maximized or sufficiently increased. If it is determined that the given cardiac characteristic (e.g., contractility) is, indeed, in the desired state, then the process may come to an end, as shown in operation 606. On the other hand, if the desired state has not been reached then control may be passed to operation 608.

Operation 608 is optional. In operation 608, one or more parameters influencing execution of the process of operation 600 are changed. For example, if operation 600 involved administration of cardiac resynchronization therapy, then one or more resynchronization parameters may be changed in operation 608. For example, an atrioventricular pacing delay parameter, biventricular delay parameter, electrode site selection parameter, etc. may be altered. Execution of operation 608 may be performed automatically by an implanted cardiac rhythm management device. Alternatively, it may be performed automatically by an external processor (e.g., accelerometer data is telemetered to a programmer or other external device; the accelerometer data is processed according to FIG. 2; the programmer automatically determines how to adjust one or more parameters on the basis of such processing, and new parameters are telemetered to the implantable device). Operation 608 may be performed manually as well (e.g., accelerometer data is telemetered to a programmer; the accelerometer data is processed according to FIG. 2; a health care professional analyzes the accelerometer data to determine how to adjust one or more parameters, and new parameters are telemetered to the implantable device). After execution of operation 608, control returns to operation 600, and the controlled process continues.

Operation 608 may be omitted entirely. For example, in the context of titration, rather than increasing or decreasing the titration rate in operation 608, the titration rate may remain constant, meaning that control returns to operation 600 and titration simply continues.

Thus, in sum, the loop defined by operations 600, 602, 604, and 608, functions to monitor and control a process, until a cardiac characteristic is observed (by virtue of detection of heart sounds with a remote accelerometer) to be in a desired state.

Figure 7:
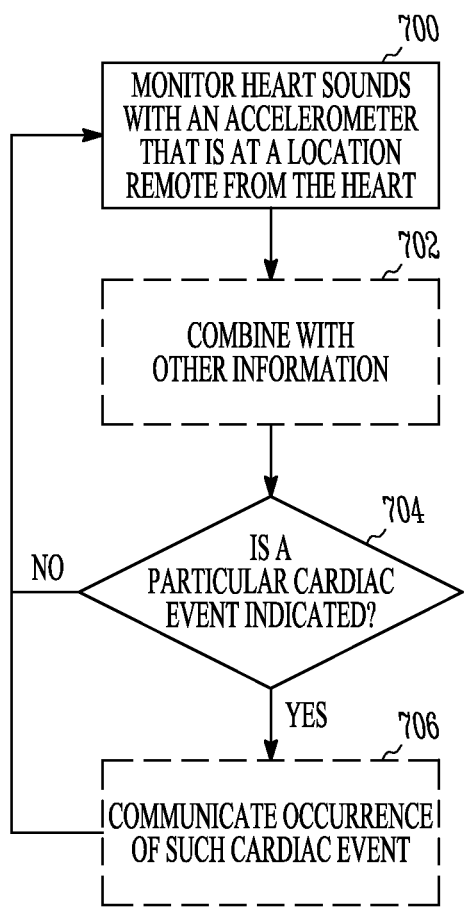
FIG. 7 depicts a method of identifying occurrence of a cardiac event, according to some embodiments of the present invention.

FIG. 7 depicts a method of identifying an occurrence of a cardiac event. Any of the acts depicted in FIG. 7 may be performed by any controller in the exemplary system of FIG. 5. The method begins with detecting heart sounds using an accelerometer that is located at a point that is remote from the heart (e.g., within an implantable device, such as the one depicted in FIG. 5), as shown in operation 700. The monitoring operation of operation 700 may include, for example, performing the acts discussed with reference to FIGS. 2-4. Thus, the median peak-to-peak amplitude exhibited by S1 heart sounds may be monitored (after being conditioned, as discussed with reference to FIGS. 2-4) to obtain information regarding the contractility of the left ventricle.

Thereafter, control may be passed to operation 702. Operation 702 is optional, and may be omitted altogether. In operation 702, the information obtained by monitoring of heart sounds in operation 700 is combined with other information (e.g., exertion level as indicated by rate of respiration and/or motion-related acceleration, etc.). The heart sound information may be combined with any of the information normally measured by a cardiac rhythm management device, for example.

Next, in operation 704, the information obtained from operations 700 and 702 (if performed) is analyzed to determine whether a cardiac event of interest is occurring. For example, the information may be analyzed to determine whether ischemia or acute heart failure decompensation is being exhibited by a patient. If no such event is detected, control is returned to operation 700, and the monitoring continues. On the other hand, if such an event is detected, control is passed to operation 706.

Operation 706 is optional. In operation 706, occurrence of the detected event is communicated. The communication may occur between an implanted cardiac management device (performing operations 700-706) and a programmer, a personal digital assistant, an access point to a network, such as a wireless or wired network, or to a wireless communication device that may forward the message to an access point for communication to a remote computing system, for example. (The programmer or personal digital assistant may relay such a message to a remote computing). Alternatively, the communication may occur between the detection routine executing on the internal controller and a history logging routine executed by the same internal controller. Thus, the occurrence of the detected event is logged, so that a health care professional may become aware of the event, for example, the next time he or she reads the data contained in the log. After execution of operation 706, control is returned to operation 700, and monitoring continues.

The method of FIG. 7 may be performed continually or at intervals. For example, a patient may be monitored for a given cardiac condition once per day (e.g., at night) or several times each day, meaning that the method of FIG. 7 would be executed once per day or several times per day.

Closed-Loop Titration System

As explained previously herein, titration of a drug to a patient can influence performance of the patient's heart. For example, an inotropic agent can improve contractility of the heart. Inotropes can be used to manage patient symptoms of advanced heart failure or HF patients (e.g., New York Heart Association or NYHA class IV patients). These patients are refractory to oral agents and intravenous (IV) therapy is typically used to prevent pulmonary edema and deterioration of the patient's hemodynamic system.

Home intravenous inotropic therapy (HT) is not only associated with improved status of hemodynamic function, decreased hospital admissions, and decreased length of hospital stay, but also with a reduction in cost of treatment. Briefly, HT therapy can involve establishing an IV access using a catheter (e.g., a catheter for percutaneous central access, or a Hickman catheter if long-term access is needed) and delivery of inotropic agents such as dobutamine or milrinone either continuously or intermittently over two to three days per week. If the patient is fluid volume overloaded, diuretic agents may also be provided by IV in combination with inotropes.

HT can be labor intensive (e.g., requiring home nurse assistance), and with HT the physician may receive limited data on the patient's treatment. Qualification for coverage for health care assistance (e.g., Medicare) may require criteria such as close monitoring of the "patient's cardiac symptoms, vital signs, weight, lab values, and response to therapy." Instead of a manually administering HT, a closed-loop sensor-based medical system may be a more cost-effective approach for meeting these criteria. The ability to titrate drug therapy based on physiological sensor data may also reduce drug adverse effects and mortality, or alternatively be more effective at weaning the patient off inotropes for destination therapy.

Implantable CRM devices and subcutaneous diagnostic devices are often indicated for HF patients. As explained previously herein, these devices can include implantable sensors (e.g., a heart sound sensor). These implantable sensors can be part of a drug infusion system that automatically provides IV therapy to the patient at the patient's home. Measurements provided by these sensors can be used to adjust the IV therapy and thereby provide a closed-loop titration system. A home-based closed-loop titration system can provide greater patient convenience and provide the clinician with the ability to remotely monitor safety and effectiveness of HT. Typical external titration devices used for HT do not use physiologic information of the patient to control titration of the drug. This may be due to the complexity that such a device would entail. The variety of cardiothoracic measurements provided using implanted sensing devices are ideally suited for control of inotropes and diuretics for home-based decongestive therapy for the treatment of advanced heart failure.

Figure 8:
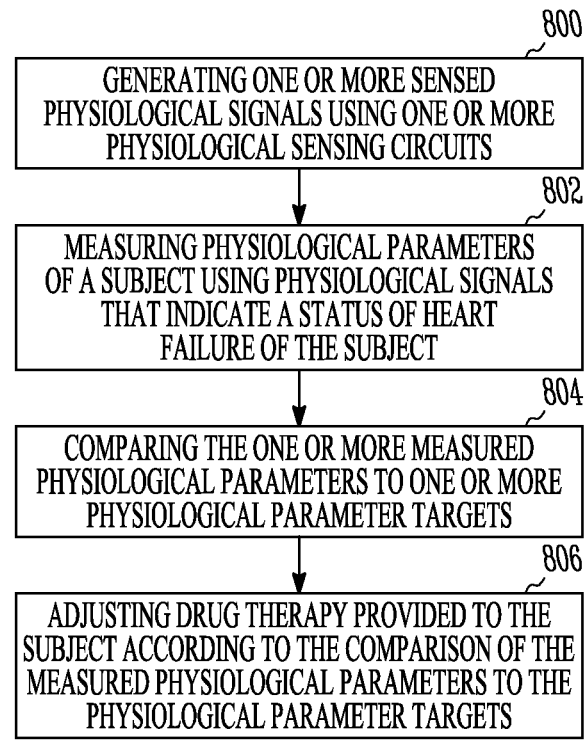
FIG. 8 depicts a flow diagram of an example of a method of operating a medical device to provide closed-loop control of titration of an agent for decongestive therapy, according to some embodiments of the present invention.

FIG. 8 shows a flow diagram of an example of a method of operating a medical device or medical device system to provide closed-loop control of titration of an agent for decongestive therapy. Any of the operations shown in FIG. 8 may be performed by a control circuit such as the controller shown in FIG. 5.

At operation 800, one or more sensed physiological signals are generated using one or more physiological sensing circuits. A physiological sensor signal includes physiological information about the patient. For example, a physiological sensor circuit may provide information about the hemodynamic system of the patient or subject. At least one of the physiological sensing circuits is implantable. As an example, the implantable physiological sensing circuit can include an implantable heart sound sensing circuit that provides an electrical heart sound signal, such as a signal that provides an indication of heart sound amplitude versus time for example. Other examples of the implantable physiological sensing circuit are described herein.

At operation 802, one or more physiological parameters of a subject are recurrently measured using the one or more sensed physiological signals. The physiological parameters indicate a status of heart failure of the patient. For example, a measure of the amplitude of the S1 heart sound provides an indication of the contractility of patient's heart. Lower S1 amplitudes are associated with more severe cases of HF.

At operation 804, the one or more measured physiological parameters are compared to one or more physical parameter targets. For example, the measured amplitude of the S1 heart sound can be compared to a target S1 amplitude value, a target range of S1 amplitude values, or a S1 amplitude target threshold value. The comparison can be made by a device that provides drug therapy to treat HF (e.g., a device that control titration of an inotropic agent to the patient).

At operation 806, drug therapy provided to the patient is recurrently adjusted by drug therapy device according to the comparison of the measured physiological parameters to the physiological parameter targets. For example, the device may cause a bolus of an inotropic agent to be delivered to the patient if the amplitude of the S1 heart sound does not satisfy a specified (e.g., programmed) amplitude threshold value.

Figure 9:
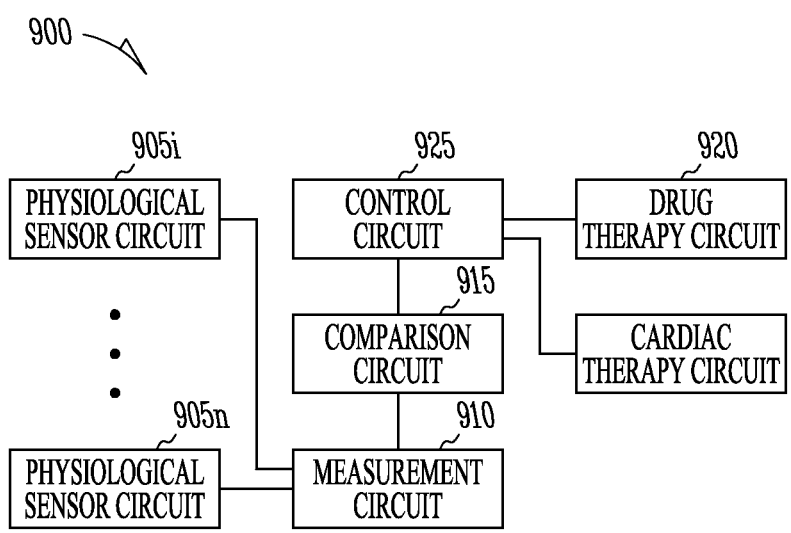
FIG. 9 depicts a block diagram of portions of an example of a system that provides closed-loop control of titration of an agent for decongestive therapy, according to some embodiments of the present invention.

FIG. 9 shows a block diagram of portions of an example of a system 900 that provides closed-loop control of titration of an agent for decongestive therapy. The system 900 includes one or more physiological sensing circuits 905i-905n. A physiological sensing circuit generates a sensed physiological signal and at least one of the physiological sensing circuits is implantable. The system 900 also includes a measurement circuit 910, a comparison circuit 915, a therapy circuit 920 and a control circuit 925. The measurement circuit 910 recurrently measures one or more physiological parameters of a subject using one or more of the sensed physiological signals. The measured physiological parameters indicate a status of heart failure of the subject.

The therapy circuit 920 controls delivery of one or more drugs to treat heart failure. The therapy circuit 920 may control delivery of a drug from a reservoir included in a medical device (e.g., a device such as a drug pump that is implantable subcutaneously), or the therapy circuit 920 may control delivery of the drug from a source external to the device (e.g., through control of an IV drug delivery sub-system). The therapy circuit 920 may control titration of at least one of an inotropic agent, a diuretic agent, an aquaretic agent, or a vasodilating agent. If the therapy circuit 920 controls an IV drug delivery sub-system, the therapy circuit may control titration of at least one of a crystalloid (e.g., saline, lactated ringers etc.) or a colloid to the patient. The comparison circuit 915 compares the one or more physiological parameter measurements provided by the measurement circuit 910 to one or more physiological parameter target values.

The control circuit 925 is in electrical communication with the comparison circuit 915 and the therapy circuit 920. The electrical communication allows signals to be communicated among the control circuit 925, the comparison circuit 915 and the therapy circuit 920 even though there may be intervening circuitry between the circuits. The control circuit 925 recurrently adjusts delivery of drug therapy to the subject according to the comparison of the measured physiological parameters to the physiological parameter targets. Thus, the system 900 provides device-based closed-loop system control of the drug therapy provided to the patient.

The control circuit 925 may perform a closed-loop algorithm that combines information from the physiological sensing circuits, and adjusts the drug infusion rate to influence or control the values of the physiological parameters. The control circuit 925 may adjust the drug infusion provided by the therapy circuit 920 using a "control to parameter range" approach, where the closed-loop algorithm changes one or more of the rate of drug infusion, a total daily infusion dose, and a drug infusion schedule (e.g., from once a day to twice a day, from twice a day to three times a day, etc.) to meet a target range of values for a physiological parameter. The control circuit 925 may adjust the drug infusion provided by the therapy circuit 920 using a "control to target" approach, where the closed-loop algorithm increases or decreases the rate of drug infusion to move a value of a physiological parameter toward a target value. The control circuit 925 may adjust the drug infusion provided by the therapy circuit 920 using "ON/OFF control," where the closed-loop algorithm initiates drug infusion when a physiological parameter does not satisfy a physiological parameter threshold value and stops the drug infusion when the physiological parameter satisfies the physiological parameter threshold value.

The response of the patient to the drug can be viewed as a "plant model" in control theory. The control circuit 925 may implement a proportional controller, a proportional integral controller, or a proportional integral derivative controller to control the drug infusion. In a simple proportional controller, the controller output is proportional to the error in a measurement of the parameter of interest, where the error is defined as the difference between the target value of the parameter of interest and the measured value of the parameter. A proportional integral (PI) control algorithm is designed to eliminate an offset associated with the proportional controller by making the controller output proportional to the amount of time the error is present. In a proportional integral derivative (PID) controller, derivative action is added to increase the speed of response and to anticipate changes. The derivative term acts on the rate of change of the error.

The inputs for the closed-loop algorithm may incorporate supervisory input from a clinician and the patient as well as the output from the physiological sensing circuits. The output of the closed-loop algorithm can be a profile for the drug infusion. The profile can be the rate of drug infusion or an amount of drug infused versus time. The feedback of the output can be a characterization of the hemodynamic response (e.g., a short term response, step response, impulse response, etc.) of the patient.

The physiological sensing circuits may be included in a combination of implantable and external devices and the system 900 may be a combination of implantable and external devices. A significant proportion of HF patients are prescribed implantable CRM devices because cardiac arrhythmias often cause adverse events in patients with advanced HF. In some examples, a CRM device implanted in the patient may include the implantable physiological sensing circuit, and an external device may include the control circuit 925, the comparison circuit 915, the measurement circuit 910, the therapy circuit 920 and an external physiological sensing circuit.

Implantable physiological sensing circuits may provide the advantage of allowing more frequent measurements of the physiological parameters, including both acute measurements of the parameters during drug infusion and chronic measurements of the parameters between infusions of the drug. One or both of acute measurements and chronic measurements of the physiological parameter can be used by the closed-loop algorithm to tailor drug therapy to the needs of the patient.

In some examples, the physiological sensing circuits 905i-905n can include an implantable heart sound sensing circuit. The heart sound sensing circuit generates a sensed heart sound signal. The heart sound signal can be an electrical signal representative of mechanical activity of the heart of the patient. Examples of a heart sound sensing circuit include an accelerometer and a microphone.

The physiological parameter measured by measurement circuit 910 of FIG. 9 may include a measure a magnitude of a heart sound (e.g., one or more of the S1, S2, S3 and S4 heart sounds). The measured physiological parameter is compared to a target value (e.g., the measured absolute magnitude value of the S1 heart sound is compared to a specified magnitude target value). The measured physiological parameter may include a time interval between a first heart sound signal feature and a second heart sound signal feature. Some examples of the interval include the interval between an S1 and S2 heart sound (e.g., the heart sound based ejection time or HSET). The control circuit 925 adjusts delivery of the drug therapy according to a comparison of the least one of the magnitude or the time interval measured in the heart sound signal to at least one of a target heart sound magnitude value or a time interval target value.

In some examples, the physiological sensing circuits include an implantable pressure sensing circuit that generates a sensed pressure signal. The pressure signal can be representative of at least one of arterial blood pressure, central venous pressure, pulmonary artery pressure, left atrial pressure, or abdominal pressure of the patient. The measurement circuit 910 provides, as the physiological parameter, a measure of at least one of arterial blood pressure, central venous pressure, pulmonary artery pressure, left atrial pressure, or abdominal pressure using the sensed pressure signal. The comparison circuit 915 provides an indication of an outcome of at least one of: a comparison of a measure of arterial blood pressure to a target arterial blood pressure, a comparison of a measure of central venous pressure to a target central venous pressure value, a comparison of a measure of pulmonary artery pressure to a target pulmonary artery pressure, a comparison of a measure of left atrial pressure to a target left atrial pressure value, or a comparison of a measure of abdominal pressure to a target value of abdominal pressure. The control circuit 925 recurrently adjusts delivery of the drug therapy according to the comparison.

In some examples, the physiological sensing circuits include an implantable cardiac activity sensing circuit (e.g., a cardiac signal sense amplifier) that generates a cardiac activity signal. The measurement circuit 910 provides, as the physiological parameter, a measure of heart rate of the patient. The comparison circuit 915 provides an indication of an outcome of a comparison of the heart rate of the subject to a target heart rate value. In some examples, the physiological sensing circuits include an implantable physical activity sensing circuit in addition to the implantable cardiac activity sensing circuit. The implantable physical activity sensing circuit generates a physical activity signal representative of physical activity of the subject. Some examples of implantable physical activity sensing circuit include an accelerometer and a vibration sensor. The measurement circuit 910 provides, as the physiological parameter, a measure of physiological response to activity of the patient (e.g., a change in heart rate or change in cardiac depolarization interval in response to a change in activity level). The comparison circuit 915 provides an indication of an outcome of a comparison of the measure of physiologic response to activity to a physiological response to activity target.

In some examples, the physiological sensing circuits include an implantable heart sound sensing circuit as described previously herein, and an electrogram circuit that generates a sensed electrogram signal or waveform. An electrogram signal is a sampled cardiac activity signal that can be sensed using implantable or subcutaneous electrodes and a cardiac signal sense amplifier. The electrogram signal is representative of electrical activity of the heart. The measurement circuit 910 may provide, as the physiological parameter, a time interval between a feature detected in the sensed heart sound signal and a feature detected in the sensed electrogram signal. Some examples include an interval between an R-wave feature (e.g., an R-wave peak) in the electrogram signal and an S1 heart sound feature (e.g., an onset of the S1 heart sound) in the heart sound signal (i.e., the heart sound based pre-ejection period or HSPEP), an interval between a Q-wave feature in the electrogram signal and an S1 heart sound feature in the heart sound signal (Q-S1 interval), an interval between an R-wave feature in the electrogram signal and an S2 heart sound feature (e.g., an onset of the S2 heart sound) in the heart sound signal (R-S2 interval), and an interval between a Q-wave feature in the electrogram signal and an S2 heart sound feature in the heart sound signal (Q-S2 interval). The control circuit 925 adjusts delivery of the drug therapy according to a comparison of the measured time interval to a time interval target value.

In some examples, the physiological sensing circuits include a respiration sensing circuit. The respiration sensing circuit may provide an electrical "respiration signal" that includes respiration information. The respiration sensing circuit may be implantable or external. An example of a respiration sensing circuit includes an implantable impedance sensing circuit, and the respiration signal may be a measured impedance signal. An example of an implantable impedance sensing circuit is an implantable transthoracic impedance sensing circuit. Transthoracic impedance can be sensed between an electrode on an implantable lead and an electrode formed on a housing of an IMD. An approach to measuring thoracic impedance is described in Hartley et al., U.S. Pat. No. 6,076,015 "Rate Adaptive Cardiac Rhythm Management Device Using Transthoracic Impedance," filed Feb. 27, 1998, which is incorporated herein by reference. Another example of the respiration sensing circuit includes a motion sensing circuit (e.g., an accelerometer) that senses motion of the thoracic cavity of the subject. The motion sensing circuit may implantable or external. Another example of the respiration sensing circuit respiration circuit includes a volume or flow sensor.

The measurement circuit 910 may extract one or more respiration parameters from the respiration signal. Some examples of a respiration parameter include a respiration rate of the subject, an inter-breath interval of the subject, a measure of variability of respiration rate of the subject, or a measure of variability of an inter-breath interval of the subject. Additional examples of a respiration parameter include tidal volume and minute ventilation calculated for the patient. In certain examples, the measurement circuit 910 can extract respiration rate from the respiration signal and determine tidal volume from the measured impedance values of the respiration signal. Minute ventilation can then be calculated using the respiration rate and tidal volume as MV=RR×TV. The comparison circuit 915 provides an indication of an outcome of a comparison of the measured respiration parameter to a respiration parameter target value.

In some examples, the physiological sensing circuits include an implantable impedance circuit that generates an impedance signal representative of intra-thoracic impedance of the patient. Intra-thoracic impedance can be sensed between an electrode on an implantable lead and an electrode formed on a housing of an IMD. A measure of intra-thoracic impedance can be useful as a surrogate measure of fluid buildup in the thorax region of the patient. The measurement circuit 910 provides a measure of intra-thoracic impedance and the comparison circuit 915 provides an indication of a comparison of the measure of intra-thoracic impedance to a target intra-thoracic impedance value.

In some examples, the physiological sensing circuits include an implantable impedance circuit that generates an impedance signal representative of intracardiac impedance of the patient. An intracardiac impedance sensing circuit may include electrodes placed within a chamber of the heart and provide an "intracardiac impedance signal" representative of intracardiac impedance versus time. The electrodes may be placed in a right ventricle of the heart and the measured intracardiac impedance waveform can be signal processed to obtain a measure of the time interval beginning with a paced or spontaneous QRS complex (systole marker) and ending with a point where the impedance signal crosses the zero axis in the positive direction following the QRS complex. The resulting time interval is inversely proportional to the contractility of the heart. Systems and methods to measure intracardiac impedance are described in Citak et al., U.S. Pat. No. 4,773,401, entitled "Physiologic Control of Pacemaker Rate Using Pre-Ejection Interval as the Controlling Parameter," filed Aug. 21, 1987, which is incorporated herein by reference in its entirety. The measurement circuit 910 can provide a measure of intracardiac impedance and the comparison circuit 915 can provide an indication of a comparison of the measure of intracardiac impedance to a target intracardiac impedance value.

In some examples, the physiological sensing circuits include an implantable sensing circuit that generates a physiological signal indicative of a level of a biochemical analyte present in the patient. Some examples of biochemical analytes include sodium, potassium, chromium, blood urea nitrogen (BUN), hematocrit, and hemoglobin. The measurement circuit 910 provides an indication of the level of the biochemical analyte, and the comparison circuit 915 provides an indication of outcome of a comparison of the indicated level of biochemical analyte to a target level of the biochemical analyte.

As explained previously herein, the system 900 of FIG. 9 can include a combination of implantable and external devices. External sensing circuits may be used to measure physiological parameters that cannot effectively be measured using implantable sensors. In some examples, the one or more physiological sensing circuits 905i-905n include at least one implantable physiological sensing circuit that provides a first sensed physiological signal, and at least one external sensing circuit configured to provide a second sensed physiological signal.

Some examples of an external sensing circuit include one or more devices that provide an indication of the patient's weight, arterial blood pressure and peripheral edema. Additional examples include external devices that provide point-of-care measurements of biochemical analytes such as brain natriuretic peptide or BNP (including an N-terminal amino acid secreted with BNP or NT-Pro-BNP), creatinine, urinalysis, etc. The measurements may be obtained using the same access site used for infusion of the drug. Further examples of external sensing circuits include external versions of the implantable sensing circuits described previously herein, such as a respiration sensing circuit, a heart sound sensing circuit, and a thoracic impedance sensing circuit.

The second sensed physiological signal provided by the external sensing circuit can be representative of at least one of weight of the patient, respiration of the patient, a heart sound of the patient, arterial blood pressure of the patient, an indication of peripheral edema of the patient, thoracic fluid present in the patient, or a level of biochemical analyte present in the patient.

The measurement circuit 910 provides a measure of a first physiological parameter using the first sensed physiological signal and a second physiological parameter using the second sensed physiological signal. The second physiological parameter includes at least one of a measured weight of the patient, a respiration parameter of the patient, a magnitude of a heart sound, a time interval between a first heart sound signal feature and a second heart sound signal feature, a measured arterial blood pressure of the patient, a measure of edema of the patient, or an indication of a level of biochemical analyte present in the patient.

The comparison circuit provides an indication of an outcome of a comparison of the first physiological parameter to a target first physiological parameter value and the second physiological parameter to a target second physiological parameter value. The control circuit 925 adjusts delivery of the drug therapy according to the outcome of the comparison of the first and second physiological parameters to the target first and second physiological parameter values.

In some examples, the measurement circuit 910, the comparison circuit 915, the therapy circuit 920, the control circuit 925 and at least one implantable physiological sensor are included in an implantable device. The implantable device can include a drug reservoir or drug pump, and the therapy circuit 920 controls delivery of drug therapy from the drug pump or reservoir. The implantable device may communicate wirelessly with an external device that provides one or both of a physiological signal sensed by the external device and a physiological parameter extracted from the sensed physiological signal. The implantable device may provide electrical cardiac therapy such as cardiac resynchronization therapy (CRT) for example. Thus, both the electrical cardiac therapy and the drug therapy can be an output of the closed-loop feedback system implemented by the system 900 to control one or more physiological parameters.

Figure 10:
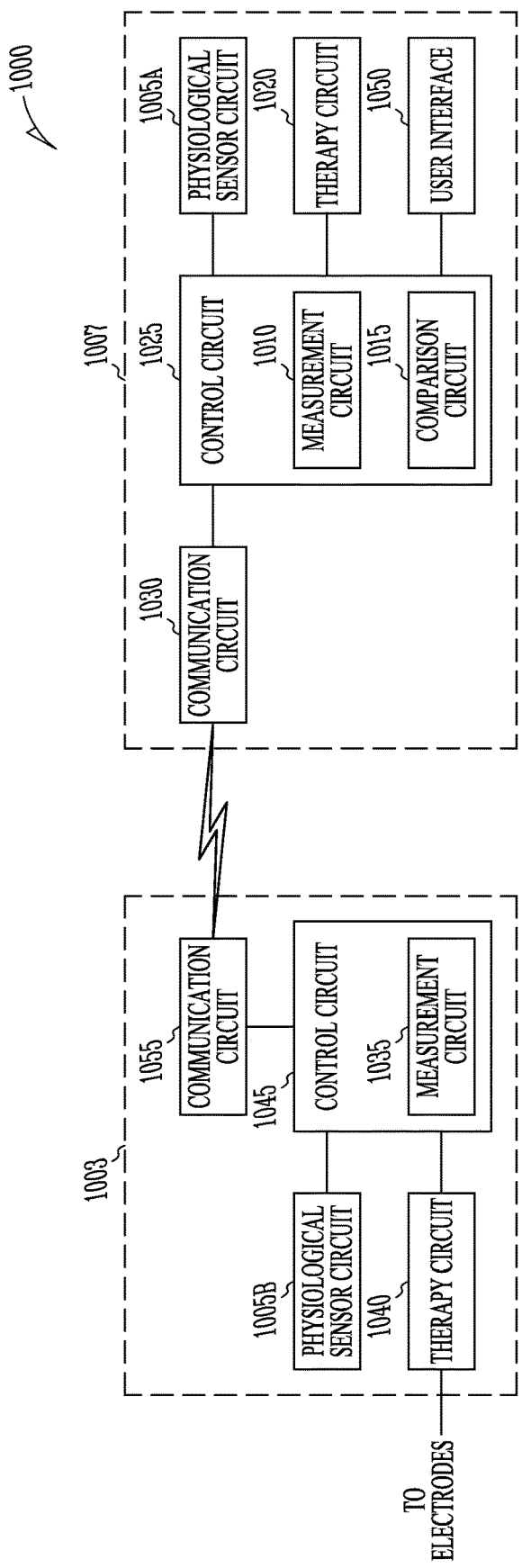
FIG. 10 depicts a block diagram of portions of another example of a system that provides closed-loop control of titration of an agent for decongestive therapy, according to some embodiments of the present invention.

FIG. 10 shows a block diagram of portions of another example of a system 1000 that provides closed-loop control of titration of an agent for decongestive therapy. The system 1000 includes an external device 1007 and an implantable device 1003. The external device 1007 includes a therapy circuit 1020 that controls delivery of one or more drugs to treat heart failure, and includes an external physiological sensing circuit 1005A.

The implantable device 1003 includes at least one implantable physiological sensing circuit 1005B. The external physiological sensing circuit 1005A and implantable physiological sensing circuit 1005B each provide a physiological signal such as the physiological signals described herein. The implantable device 1003 and the external device 1007 include communication circuits 1055 and 1030 respectively to communicate information between the implantable device 1003 and the external device 1007. The communication is wireless and may include RF communication or inductive telemetry.

The implantable device may communicate a representation (e.g., a digitized representation) of the physiological signal sensed by the implantable physiological sensing circuit 1005B to the external device 1007. The external device 1007 includes a measurement circuit 1010 that recurrently measures one or more physiological parameters using one or more of the physiological signals sensed by the external physiological sensing circuit 1005A and implantable physiological sensing circuit 1005B. In some examples, the implantable device 1003 includes a measurement circuit 1035 that measures a physiological parameter using the physiological signal sensed by the implantable physiological sensing circuit 105B and communicates a measured physiological parameter to the external device 1007.

The external device 1007 includes a comparison circuit 1015 that compares the one or more physiological parameter measurements to one or more physiological parameter target values. The external device 1007 also includes a control circuit 1025 that recurrently adjusts delivery of drug therapy to the patient according to the comparison of the measured physiological parameters to the physiological parameter targets.

In some examples, the implantable device 1003 includes a therapy circuit 1040 that provides electrical cardiac therapy to the patient, such as cardiac resynchronization therapy for example. According to the comparison of the measured physiological parameters to the physiological parameter targets by the comparison circuit 1015 of the external device 1007, the control circuit 1025 may communicate an indication to initiate or adjust the electrical cardiac therapy delivered by the implantable device 1003. The implantable device 1003 may include a control circuit 1045 to manage the electrical cardiac therapy. Thus, the electrical cardiac therapy provided by the implantable device 1003 can be part of the closed-loop feedback system implemented by the system 1000.

The therapy circuit 1020 of external device 1007 may control intravenous delivery of the drug therapy to the patient (e.g., the external device may be an IV drug infusion system). The external device may include a user interface 1050 to receive input from the patient to include patient physiology in the control of the drug therapy. For instance, the user interface 1050 may include a visual analog scale to test the response of the patient. The response may be captured by the external device 1007 and incorporated into the control algorithm implemented by the control circuit 1025.

In some examples, the external device 1007 is able to communicate with a remote third device using the communication circuit 1030 or a separate communication circuit. The third device may be a remote monitoring system that provides patient monitoring and management of patient cardiac disease. The communication between the external device and the remote system may be RF communication via a local or person area network, or the communication may be via a more extensive communication network such as the internet or a cellular phone network. The remote monitoring system may receive physiological information and a drug therapy delivery profile from the external device 1007 and display the information to a physician or include the information in a report for review by a physician.

The examples of closed-loop drug titration devices, methods and systems provided herein can make full use of all the physiological information available regarding the patient. The systems can be implemented in the patient's home and thus provide greater patient convenience. They also allow give the clinician the ability to remotely monitor safety and effectiveness of HT. Closed-loop drug therapy may improve patient treatment at lower cost.

Additional Notes

Embodiments of the invention may be implemented in one or a combination of hardware, firmware, and software. Embodiments of the invention may also be implemented as instructions stored on a machine-readable medium, which may be read and executed by at least one processor to perform the operations described herein. A machine-readable medium may include any mechanism for storing or transmitting information in a form readable by a machine (e.g., a computer). For example, a machine-readable medium may include read-only memory (ROM), random-access memory (RAM), magnetic disc storage media, optical storage media, flash-memory devices, electrical, optical, acoustical or other form of propagated signals (e.g., carrier waves, infrared signals, digital signals, etc.), and others.

The Abstract is provided to comply with 37 C.F.R. Section 1.72(b) requiring an abstract that will allow the reader to ascertain the nature and gist of the technical disclosure. It is submitted with the understanding that it will not be used to limit or interpret the scope or meaning of the claims.

In the foregoing detailed description, various features are occasionally grouped together in a single embodiment for the purpose of streamlining the disclosure. This method of disclosure is not to be interpreted as reflecting an intention that the claimed embodiments of the subject matter require more features than are expressly recited in each claim. Rather, as the following claims reflect, inventive subject matter lies in less than all features of a single disclosed embodiment. Thus, the following claims are hereby incorporated into the detailed description, with each claim standing on its own as a separate preferred embodiment.

The invention claimed is:

1. An apparatus comprising:
a cardiac therapy circuit configured to provide electrical cardiac therapeutic stimuli to treat cardiac arrhythmia; including biventricular pacing therapy;
a drug therapy circuit configured to control delivery of one or more of diuretic agents and inotropic agents to treat heart failure;
a cardiac signal sensing circuit configured to generate a sensed cardiac activity signal;
a measurement circuit configured to recurrently measure a first physiological parameter of a subject using the sensed cardiac activity signal, wherein the first physiological parameter indicates a status of heart failure of the subject;
a comparison circuit configured to compare a measured value of the first physiological parameter to a first physiological parameter target value; and
a control circuit in electrical communication with the comparison circuit, the drug therapy circuit, and the cardiac therapy circuit, and configured to initiate closed loop delivery of drug therapy to treat heart failure of the subject using the drug therapy circuit, initiate measurement of the first physiological parameter after a specified number of cardiac cycles after the delivery, recurrently initiate a comparison of the measured value of the first physiological parameter to the first physiological parameter target value, recurrently adjust the drug therapy to move the measured value of the first physiological parameter toward the target value according to the comparison, and change at least one of a biventricular pacing delay parameter or a cardiac electrode site selection parameter to move the measured value of the first physiological parameter toward the target value.

2. The apparatus of claim 1, including:
an external sensing circuit configured to provide a sensed physiological signal representative of at least one of: weight of the subject, respiration of the subject, a heart sound of the subject, arterial blood pressure of the subject, an indication of peripheral edema of the subject, thoracic fluid present in the subject, or a level of biochemical analyte present in the subject, wherein the measurement circuit is configured to measure an external physiological parameter that includes at least one of a measured weight of the subject, a respiration parameter of the subject, a magnitude of a heart sound, a time interval between a first heart sound signal feature and a second heart sound signal feature, a measured arterial blood pressure of the subject, a measure of edema of the subject, or an indication of a level of biochemical analyte present in the subject, wherein the comparison circuit is configured to compare the first physiological parameter to a target first physiological parameter value and the external physiological parameter to a target second physiological parameter value and provide an indication of an outcome of the comparing, wherein the control circuit is configured to adjust delivery of the drug therapy and the cardiac therapy according to a comparison of the first physiological parameter and the second physiological parameter to the target first and second physiological parameter values.

3. The apparatus of claim 1, wherein the control circuit is configured to adjust at least one parameter of cardiac resynchronization therapy (CRT) according to the comparison of the measured first physiological parameter to the first physiological parameter target.

4. The apparatus of claim 1, wherein the control circuit is configured to adjust an atrioventricular pacing delay parameter according to the comparison of the measured first physiological parameter to the first physiological parameter target.

5. The apparatus of claim 1, including an implantable sensing circuit configured to generate a physiological signal indicative of a level of a biochemical analyte present in the subject, wherein the measurement circuit is configured to measure the level of biochemical analyte, wherein the comparison circuit is configured to compare the first physiological parameter to the target first physiological parameter value and compare the level of biochemical analyte to a target biochemical analyte level, and wherein the control circuit is configured to adjust delivery of the drug therapy and the cardiac therapy according to a comparison of the first physiological parameter to the target first physiological parameter value and compare the level of biochemical analyte to the target biochemical analyte level.

6. The apparatus of claim 1, including an implantable heart sound sensing circuit configured to generate a sensed heart sound signal, wherein the measurement circuit is configured to measure at least one heart sound parameter using the sensed heart sound signal and the comparison circuit is configured to compare the measured heart sound parameter to a target heart sound parameter value, and wherein the control circuit is configured to adjust the drug therapy and adjust electrical cardiac therapy according to the comparison of the measured heart sound parameter to the target heart sound parameter value and the measured first physiological parameter to the first physiological parameter target value.

7. The apparatus of claim 1, wherein the measurement circuit is configured to measure a time interval between a feature of the sensed cardiac activity signal and a feature of the heart sound signal, and wherein the control circuit is configured to adjust delivery of the drug therapy and the cardiac therapy according to a comparison of the measured time interval to a time interval target value.

8. The apparatus of claim 1, wherein the drug therapy circuit is configured to control titration of at least one of a diuretic agent, an aquaretic agent, or a vasodilating agent to the subject according to the comparison.

9. The apparatus of claim 1, wherein the drug therapy circuit is configured to control delivery of at least one of a crystalloid or a colloid to the subject according to the comparison.

10. A method of operating a medical device system, the method comprising:
   recurrently measuring, using an implantable medical device, a first physiological parameter of a subject using a sensed cardiac activity signal, wherein the first physiological parameter indicates a status of heart failure of the subject; and
   delivering closed loop device-based drug therapy to the subject, the closed-loop device-based drug therapy including:
   initiating delivery of the drug therapy, initiating measurement of the first physiological parameter after a specified number of cardiac cycles after the delivery of drug therapy, recurrently initiating a comparison of measured value of the first physiological parameter to a first physiological parameter target value, adjusting the drug therapy to move the measured value of the first physiological parameter toward the target value, and adjusting at least one of a biventricular pacing delay parameter or a cardiac electrode site selection parameter to move the measured value of the first physiological parameter toward the target value according to a comparison using the measurement.

11. The method of claim 10, including:
   measuring, with a sensing circuit external to the patient, an external physiological parameter that includes at least one of a measured weight of the subject, a respiration parameter of the subject, a magnitude of a heart sound, a time interval between a first heart sound signal feature and a second heart sound signal feature, a measured arterial blood pressure of the subject, a measure of edema of the subject, or an indication of a level of biochemical analyte present in the subject;
   comparing the first physiological parameter to a target first physiological parameter value and comparing the external physiological parameter to a target second physiological parameter value; and
   adjusting delivery of the drug therapy and the cardiac therapy according to a comparison of the first physiological parameter and the second physiological parameter to the target first and second physiological parameter values.

12. The method of claim 10, wherein adjusting electrical cardiac therapy includes adjusting at least one parameter of cardiac resynchronization therapy (CRT) according to the comparison of the measured first physiological parameter to the first physiological parameter target.

13. The method of claim 10, wherein adjusting electrical cardiac therapy includes an atrioventricular pacing delay parameter according to the comparison of the measured first physiological parameter to the first physiological parameter target.

14. The method of claim 10, including:
   measuring a level of biochemical analyte present in the subject using an implantable analyte sensing circuit,
   comparing the first physiological parameter to the target first physiological parameter value and compare the level of biochemical analyte to a target biochemical analyte level; and
   adjusting delivery of the drug therapy and the cardiac therapy according to a comparison of the first physiological parameter to the target first physiological parameter value and compare the level of biochemical analyte to the target biochemical analyte level.

15. The method of claim 10, including:
   measuring at least one heart sound parameter using a heart sound signal sensed with an implantable heart sound signal sensing circuit;
   comparing the measured heart sound parameter to a target heart sound parameter value; and
   adjusting the drug therapy and adjust electrical cardiac therapy according to the comparison of the measured heart sound parameter to the target heart sound parameter value and the measured first physiological parameter to the first physiological parameter target value.

16. The method of claim 10, including measure a time interval between a feature of asensed cardiac activity signal and a feature of a sensed heart sound signal, and adjusting delivery of the drug therapy and the cardiac therapy according to a comparison of the measured time interval to a time interval target value.

17. The method of claim 10, wherein adjusting device-based drug therapy includes controlling titration of at least one of a diuretic agent, an aquaretic agent, or a vasodilating agent to the subject according to the comparison.

18. The method of claim 10, wherein adjusting device-based drug therapy includes controlling delivery of at least one of a crystalloid or a colloid to the subject according to the comparison.

* * * * *